(12) United States Patent
Campanella et al.

(10) Patent No.: US 10,822,371 B2
(45) Date of Patent: Nov. 3, 2020

(54) SOLID PHASE SYNTHESIS OF NIR FLUORESCENT PROBE

(71) Applicant: BRACCO IMAGING S.P.A., Milan (IT)

(72) Inventors: Raphael Campanella, Échenevex (FR); Anthony Clouet, Prévessin-Moëns (FR); Luciano Lattuada, Cassina De'Pecchi (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 16/769,633

(22) PCT Filed: Dec. 5, 2018

(86) PCT No.: PCT/EP2018/083590
§ 371 (c)(1),
(2) Date: Jun. 4, 2020

(87) PCT Pub. No.: WO2019/110639
PCT Pub. Date: Jun. 13, 2019

(65) Prior Publication Data
US 2020/0317722 A1    Oct. 8, 2020

(30) Foreign Application Priority Data
Dec. 6, 2017 (EP) ................................ 17205693

(51) Int. Cl.
*C07K 1/10* (2006.01)
*C07K 1/06* (2006.01)

(52) U.S. Cl.
CPC ............. *C07K 1/061* (2013.01); *C07K 1/10* (2013.01)

(58) Field of Classification Search
None
See application file for complete search history.

(56) References Cited

U.S. PATENT DOCUMENTS

2003/0191049 A1    10/2003    Amblard et al.

FOREIGN PATENT DOCUMENTS

| WO | 2006092722 A1 | 9/2006 | |
|----|---------------|--------|--|
| WO | 2006095234 A2 | 9/2006 | |
| WO | WO-2006095234 A2 * | 9/2006 | ............. A61P 35/00 |
| WO | 2016097317 A1 | 6/2016 | |

OTHER PUBLICATIONS

Qi et al. RSC Adv., (2016) 6, 74560-74566.*
Qi et al. RGD conjugated, Cy5.5 labeled polyamidoamine dendrimers for targeted near-infrared fluorescence imaging of esophageal squamous cell carcinoma RSC Adv., 6, 74560-74566 (2016).*
Albericio F. et al., "Preparation and Application of the 5-(4-(9-Fluorenylmethyloxycarbonyl)aminomethyl-3,5 dimethoxyphenoxy)-valeric Acid (PAL) Handle for the Solid-Phase Synthesis of C-Terminal Peptide Amides under Mild Conditions," J. Org. Chem., 55:3730-3743 (1990).
Barany, G. et al., "Solid-phase peptide synthesis: a silver anniversary report," Int. J. Peptide Protein Res., 30:705-739 (1987).
Bonner, A.G. et al., "Solid-phase precipitation and extraction, a new separation process applied to the isolation of synthetic peptides," J. Peptide Res., 57:48-58 (2001).
Coin et al., "Solid-phase peptide synthesis: from standard procedures to the synthesis of difficult sequences," Nature Protocols, 2:3247-3256 (2007).
Conti, Laura et al., "Optical imaging detection of microscopic mammary cancer in ErbB-2 transgenic mice through the DA364 probe binding [alpha]V[beta]3 integrins", Contrast Media & Molecular Imaging, 8:350-360 (2013).
Delforge et al., "Solid-phase synthesis of tailed cyclic peptides: The use of alpha-allyl-protected aspartic acid leads to aspartimide and tetramethylguanidinium formation," Letters in Peptide Science, 3:89-97 (1996).
El-Faham, A. et al. "Peptide Coupling Reagents, More than a Letter Soup," Chem Rev., 111:6557-6602 (2011).
Flouzat C. et al., "Solid-phase synthesis of 'head-to-side chain' cyclic tripeptides using allyl deprotection," Tetrahedron Lett., 38:1191-1194 (1997).
Greene, T.W., "Protective groups in organic synthesis," John Wiley & Sons, Inc. (2007).
Grieco P. et al., "Preparation of 'side-chain-to-side-chain' cyclic peptides by Allyl and Alloc strategy: potential for library synthesis," J. Peptide Res., 57:250-256 (2001).
Huang H.et al., "A cleavage cocktail for methionine-containing peptides," J.Peptide Res. 53:548-553 (1999).
International Search Report and Written Opinion for PCT/EP2018/083590, dated Jan. 25, 2019.
Joshi B.P. et al. "Design an synthesis of near-infrared peptide for in vivo molecular imaging of HER2," Bioconjugate Chem. 27:481-494 (2016).
Kates S.A. et al., "A novel, convenient, three-dimensional orthogonal strategy for solid-phase synthesis of cyclic peptides," Tetrahedron Lett., 33:1549-1552 (1993).
King, D. et al., "A cleavage method which minimizes side reactions following Fmoc solid phase peptide synthesis," Int. J. Peptide Protein Res., 36:255-266 (1990).
Lanzardo, Stefania, et al. "A new optical imaging probe targeting alpha-v-beta-3 integrin in glioblastoma xenografts," Contrast Media and Molecular Imaging, 6:449-458 (2011).
Manzoni et al ., "Functionalized Azabicycloalkane Amino Acids by Nitrone 1,3-Dipolar Intramolecular Cycloaddition," J.Org.Chem. 70(10):4124-4132 (2005).
Manzoni, Leonardo et al., "Cyclic RGD-Containing Functionalized Azabicycloalkane Peptides as Potent Integrin Antagonists for Tumor Targeting," ChemMedChem, 4:615-632 (2009).

(Continued)

*Primary Examiner* — Jeanette M Lieb
(74) *Attorney, Agent, or Firm* — Vivicar Law, PLLC

(57) ABSTRACT

The present invention discloses a solid-phase process for the preparation of a Near Infra-Red (NIR) fluorescent probe characterized by an aza-bicycloalkane based cyclic peptide labelled with a Cy5.5 dye moiety and used in the guided surgery of tumors and pathologic regions.

17 Claims, No Drawings

(56) References Cited

OTHER PUBLICATIONS

Merrifield et al., "Solid Phase Peptide Synthesis. I. The Synthesis of a Tetrapeptide," J.Am.Chem.Soc., 85:2149-2154 (1963).
Quan, Tian W. et al., "Mechanisms of Staudinger Reactions within Density Functional Theory," J.Org. Chem. 69:4299-4308 (2004).
Sole', N.A. et al., "Optimization of Solid-Phase Synthesis of [Ala8]-dynorphin A," J. Org. Chem., 57:5399-5403 (1992).
Stawikowski et al., "Introduction to Peptide Synthesis," Curr. Protoc. Protein Sci., Chapter 18, pp. 1-17 (2013).
Trzeciak, A. et al., "Synthesis of 'head to tail' cyclized peptides on solid support by FMOC chemistry," Tetrahedron Lett., 33:4557-4560 (1992).
Valeur, E. et al., "Amide bond formation: beyond the myth of coupling reagents," Chem. Soc. Rev., 38:606-631 (2009).

\* cited by examiner

SOLID PHASE SYNTHESIS OF NIR FLUORESCENT PROBE

CROSS-REFERENCE TO RELATED APPLICATIONS

This application is the national stage application of corresponding international application number PCT/EP2018/083590, filed Dec. 5, 2018, which claims priority to and the benefit of European application no. 17205693.9, filed Dec. 6, 2017, all of which are hereby incorporated by reference in their entirety.

FIELD OF THE INVENTION

The present invention relates to the field of optical imaging. More particularly, it relates to a solid-phase process of synthesis of a Near-InfraRed (NIR) fluorescent probe (known as "DA364") comprising an aza-bicycloalkane based cyclic peptide labelled with a Cy5.5 dye moiety and used in the guided surgery of tumors and pathologic regions.

BACKGROUND OF THE INVENTION

Near-infrared fluorescence (NIRF) is a powerful tool for imaging of both physiological and pathological conditions, as well as for visualization and guidance during surgery. In fact, NIR fluorescence light has the advantages of penetrating tissues up to several centimeters, reducing scattering and maximizing the signal-to-background contrast provided by exogenous NIR contrast agents. For instance, it can be used to quantify the composition of tumoral tissue in vivo and to discern tumors from background contrast variations.

For these reasons, several diagnostic agents comprising a NIR moiety have been developed in the last years to image target-containing tissues in vivo. Among the widely used near infrared dyes, the fluorophore Cy5.5, emitting at about 695 nm, has been conjugated with some targeting moieties and evaluated as fluorescent probe for real time in vivo imaging with NIRF (see for instance Joshi B. P. et al., *Bioconjugate Chem.* 2016, 27, 481-494).

The conjugation to biomarkers provides for a more specific binding and better uptake and retention. Among the targeting moieties suitable for conjugation with NIRF probes, several antibodies or peptidic sequences specific for a particular target can be cited. A widely used biochemical tool is, for instance, the tripeptide RGD (Arg-Gly-Asp), which is selectively recognized by transmembrane receptors integrins.

The present invention relates, in the field of optical imaging, to a fluorescent molecule conjugated to a peptidomimetic that targets integrin-overexpressing tumors. More specifically, it relates to an improved process of synthesis of a Near Infra-Red (NIR) fluorescent probe known as DA364 (see formula I below) comprising an aza-bicycloalkane based cyclic peptide RGD conjugated to a Cy5.5 dye moiety:

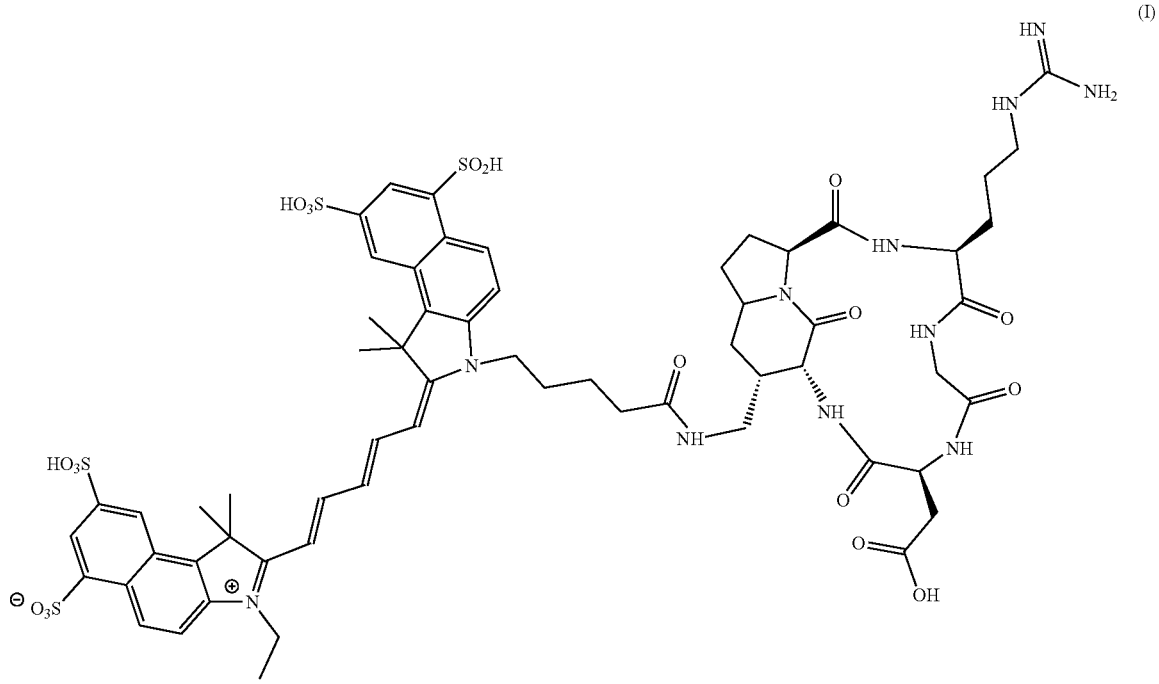

The use of DA364 in the intraoperative imaging has been effectively studied. In particular, it has been shown that the above compound of formula (I) can provide a real-time detection and demarcation of tumor margins during the NIR-fluorescence imaging guided curative surgery of tumors and pathologic regions (see for instance Conti L. et al., *Contrast Media Mol. Imaging* 2013, 8, 350-360; Lanzardo et al., *Contrast Media Mol. Imaging* 2011, 6, 449-458 and WO2016/097317 A1 in the name of the same Applicant).

This specific compound has been firstly described in Lanzardo et al., *Contrast Media Mol. Imaging* 2011, 6, 449-458, wherein the conditions for its preparation are disclosed. The synthesis of DA364, as therein described, involves the reaction of succinimidyl ester Cy5.5-NHS with the amino moiety of a cyclic peptidomimetic (cRGD), obtained after catalytic reduction of the corresponding azide compound. The preparation of the azide intermediate, or its stereoisomers, was formerly disclosed in patent applications WO2006/095234 A2 in the name of the same applicant and WO2006/092722 A1 in the name of Universitá degli Studi Milano. In particular, WO2006/095234 A2 reports a class of novel 6,5-aza-bicycloalkane based cyclic peptides acting as targeting moiety able to selectively bind to integrin receptors and shows a scheme of preparation of 6,5-trans-aza-bicycloalkane-cRGD compounds conjugated with a biologically active moiety or an imaging detectable moiety (see FIGS. 3 and 5 and pages 41-48 of the description).

Artificial polypeptides made in part of nonpeptide oligomers of amino acids are described in US 2003/191049 A1 in the name of Muriel Amblard et al.

The preparation of functionalized azabicycloalkane amino acids is disclosed in Manzoni et al., *J. Org. Chem.* 2005, 70 (10), 4124-4132, while paper Manzoni et al., *Chem. Med. Chem.* 2009, 4, 615-632 describes the preparation of the RGD-containing functionalized azabicycloalkane peptides, starting from the azabicycloalkane scaffolds through linear peptide synthesis in solution, followed by cyclization of the RGD chain. The above cited processes represent the currently used procedure in solution for the preparation of DA364, which is summarized in the following Schemes 1 and 2.

This procedure comprises the linear peptide synthesis in solution followed by cyclization, between Gly and Asp residues; formation of the azido moiety by mesylate displacement; hydrogenation of the azido to the corresponding amino function; and side chains deprotection. Afterwards the cRGD-azabicycloalkane-NH₂ is conjugated with the fluorophore Cy5.5-NHS ester.

Scheme 1

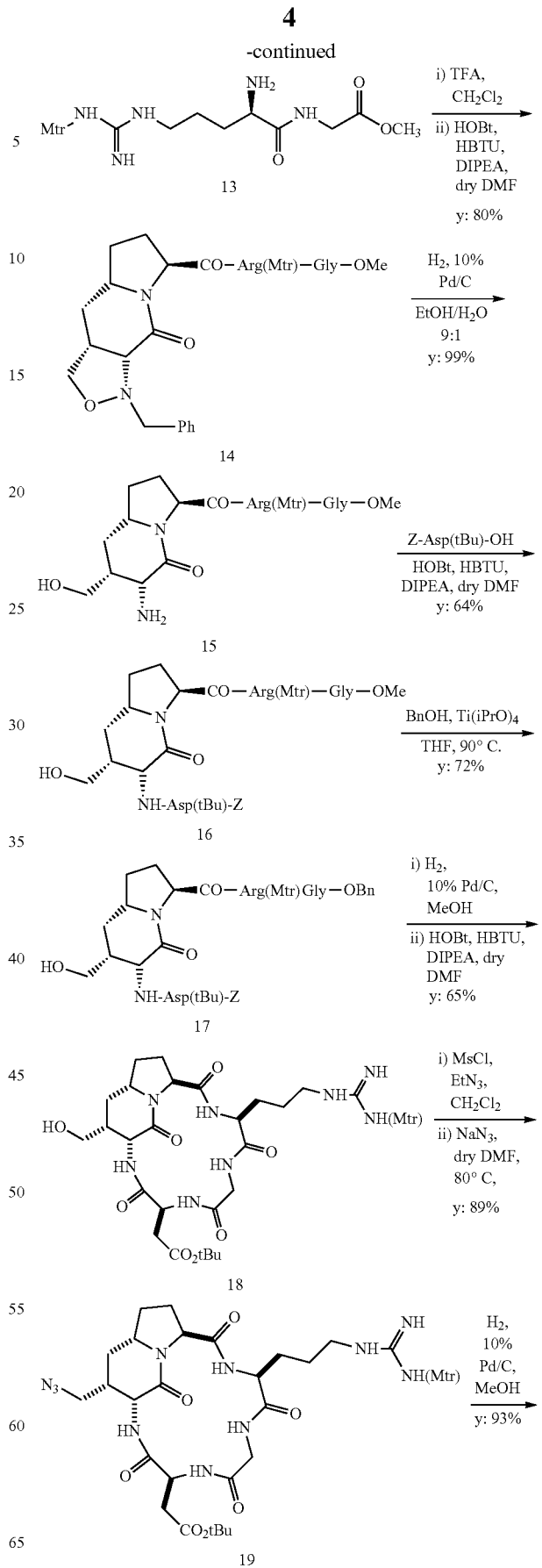

5
-continued
6
-continued
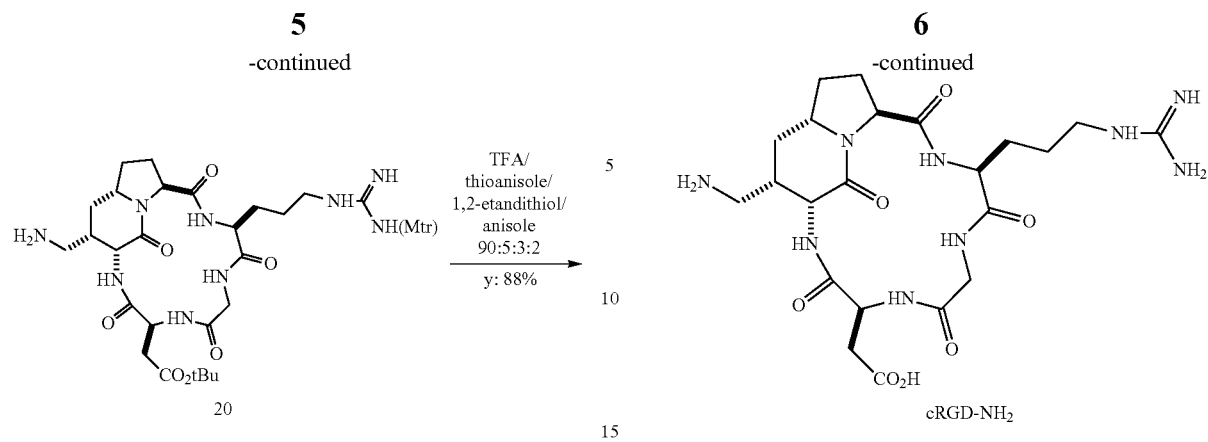
Scheme 2
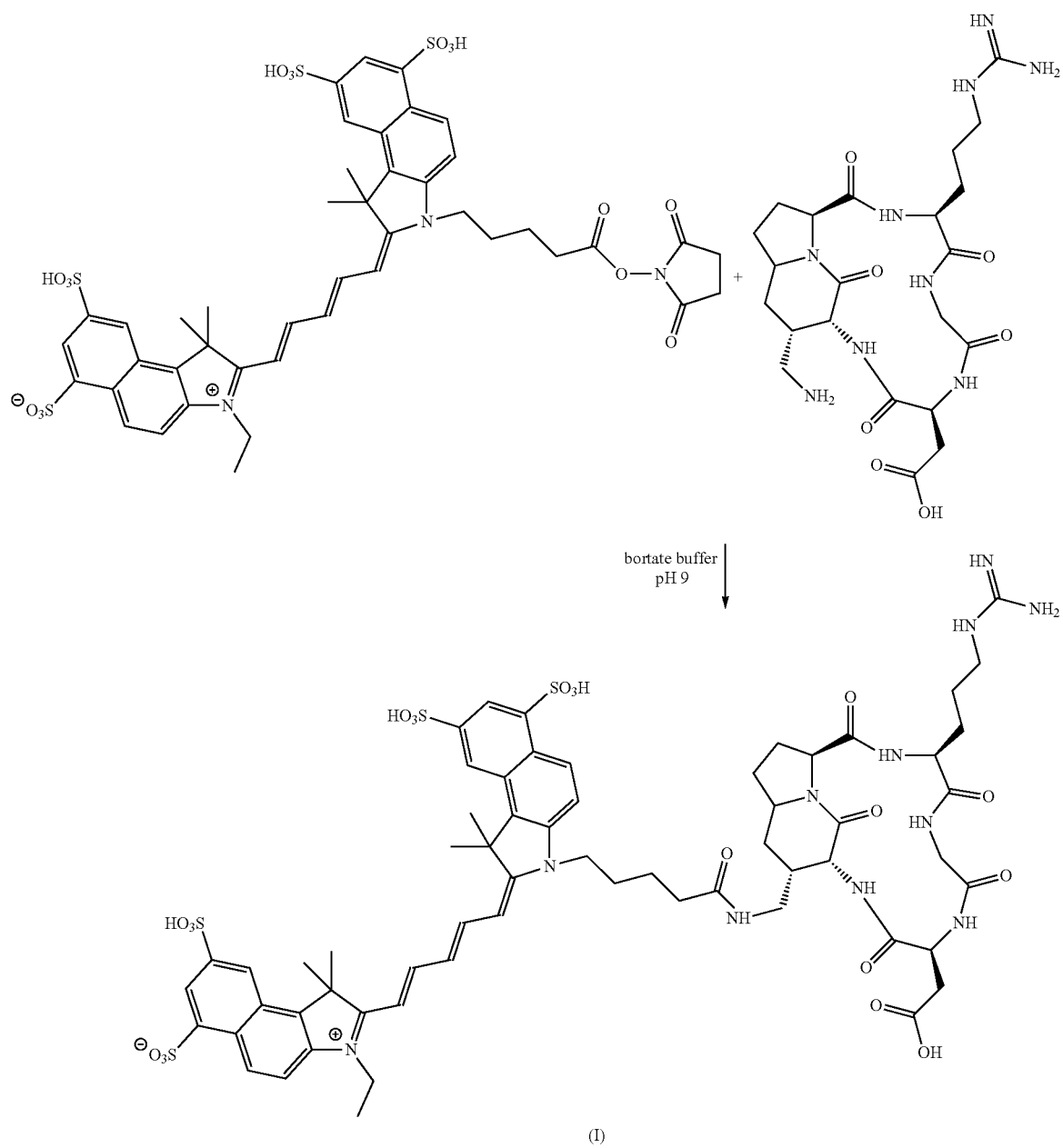

The above process has however several drawbacks in terms of yield, time and cost. In fact, the overall synthesis of DA364 represents a long process requiring a substantially high number of reaction steps (typically at least 20), lengthy preparation time (in terms of weeks) and relatively low overall yields.

For instance, at least four weeks are necessary to perform the first part of the process, prior to fluorophore conjugation, and additional days are required for the coupling to Cy5.5 and work-up of the final product, obtained with a very low recovery.

It has now been found that such compound DA364 can be conveniently synthesized using a solid-phase synthesis on an appropriate solid support.

BRIEF SUMMARY OF THE INVENTION

Object of the present invention is a new procedure of synthesis, based on a solid-phase synthetic approach, for the preparation of a cRGD-Cy5.5 conjugate of formula (I), as defined above, which has been found surprisingly advantageous for the reduction of times and the remarkable improvement of the yields.

In fact, the new process described herein allows to obtain the final product in short time (typically few days), including the purification and lyophilization steps, and to achieve overall recoveries up to 45% (considering to carry out the synthesis on a batch size of about 3 g).

Specifically, among the several advantages that can be achieved by means of the present new process it is worth to mention the simplification of the overall synthetic procedure (less number of steps with respect to the current synthesis in solution); automation of the reaction steps with consequent benefit to scaling-up of the process and industrial purposes; removal of the purification steps after completion of the intermediate chemical reactions; and minimization of product losses during synthesis. In fact, being accomplished automatically, the above synthesis process can be run 7 days a week and with a minimum human intervention.

Another advantage of this approach over the current synthesis is that the conjugation of the aza-bicycloalkane cyclic peptide RGD to the dye is performed directly on resin, without the need of a prior peptide cleavage and additional purification. As a result, this new process greatly increases the final yield and decreases the overall production time.

Therefore, according to the several benefits provided by the present invention, the synthesis of DA364 from first amino acid attachment until the final product (prior to purification) can be prepared in a remarkably shorter time with respect to the current established protocol.

Furthermore, the amount of resources and solvents used in this new process is greatly reduced due to a significant reduction of purification steps to only one, realized at the end of the synthesis.

The present invention can thus overcome the disadvantages of the current methods and make the preparation of DA364 suitable for scaling-up and industrial application.

DETAILED DESCRIPTION OF THE INVENTION

Accordingly, it is a first object of the present invention a process on solid support for the preparation of a cRGD-Cy5.5 conjugate of formula (I)

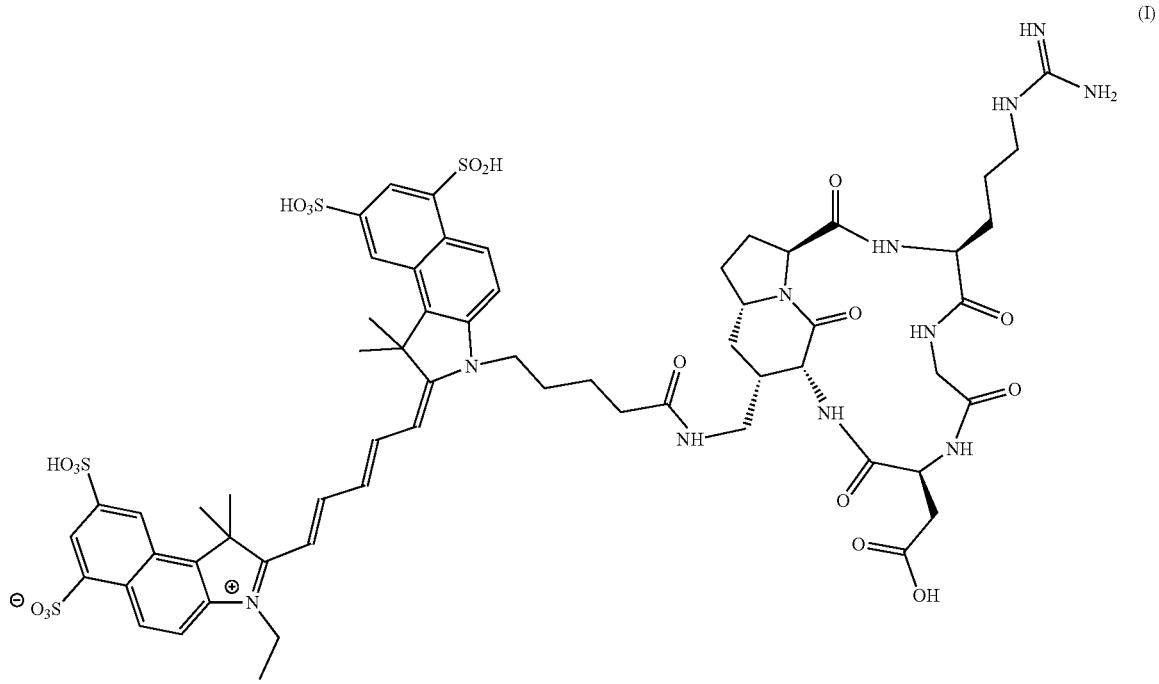

which comprises the steps of:
a) synthesising a tripeptide of formula (II) on a solid support

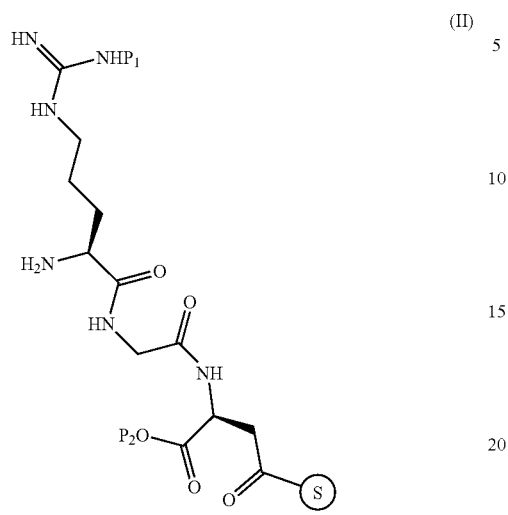

wherein $P_1$ and $P_2$ are suitable protecting groups and S is the solid support;
b) coupling of the tripeptide of formula (II) linked to the solid support with an aza-bicycloalkane of formula (III)

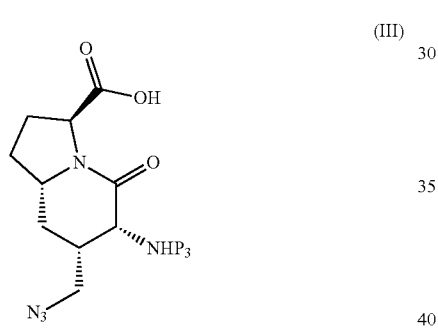

wherein $P_3$ is a suitable protecting group, to provide a compound of formula (IV)

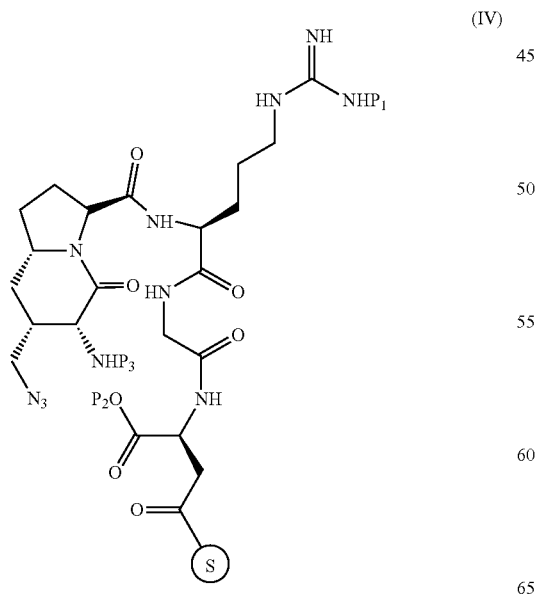

wherein $P_1$, $P_2$, $P_3$ and S are as defined above;

c) removing the protecting groups $P_2$ and $P_3$ from compound (IV) to provide a compound of formula (V)

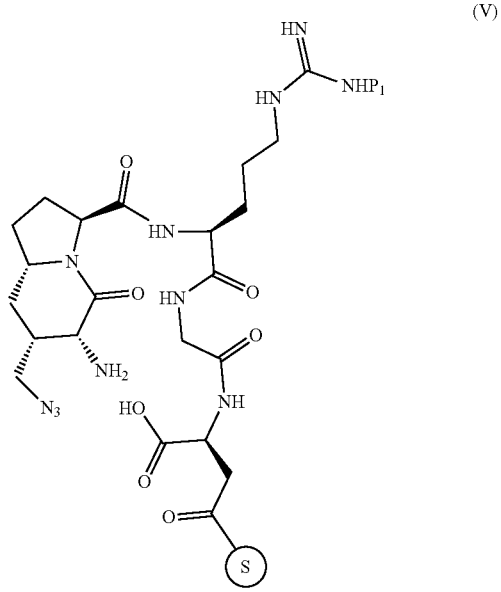

wherein $P_1$ and S are as defined above;
d) performing an intramolecular cyclization to provide a compound of formula (VI)

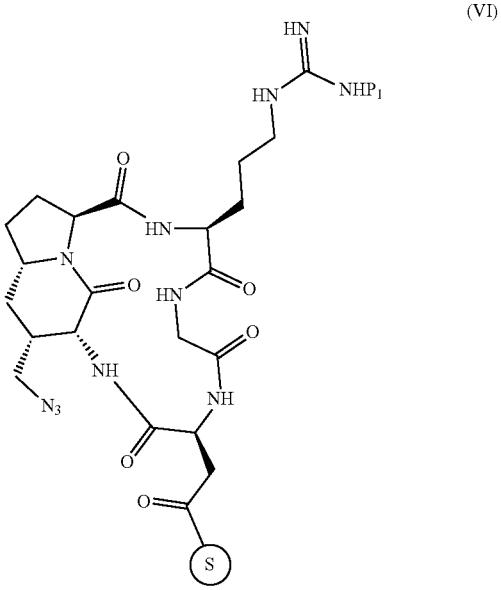

wherein $P_1$ and S are as defined above;
e) subjecting the resulting compound of formula (VI) to a reduction reaction to provide a corresponding amino-derivative of formula (VII)

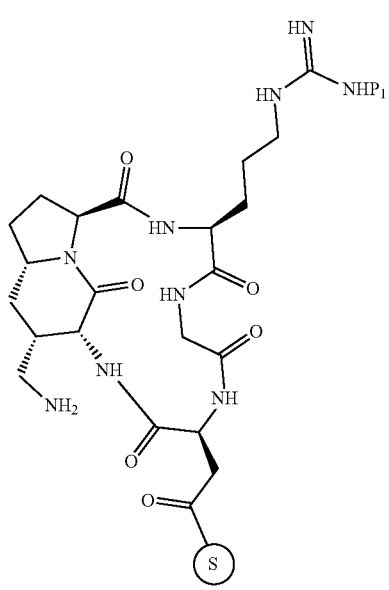
(VII)
wherein P₁ and S are as defined above;
f) conjugating of the resulting compound of formula (VII) with a compound of formula (VIII)
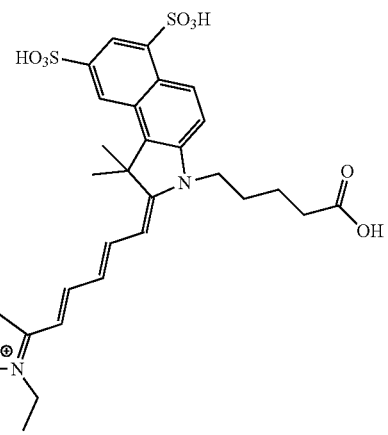
(VIII)
to obtain a compound of formula (IX)
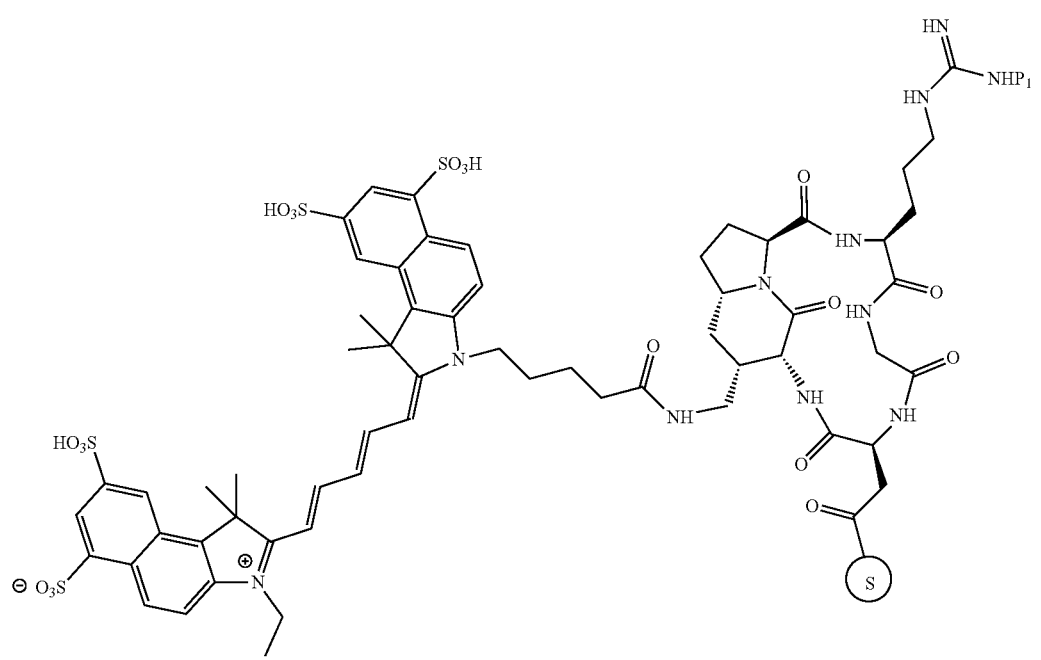
(IX)
wherein P₁ and S are ad defined above;

g) removing the protecting group P₁ and cleavaging the peptido-like compound (IX) from the solid support S to obtain the compound of formula (I) as defined above.
Accordingly, the solid-phase synthesis method of the present invention may be summarized by the following reaction Schemes 3 and 3a.
Scheme 3
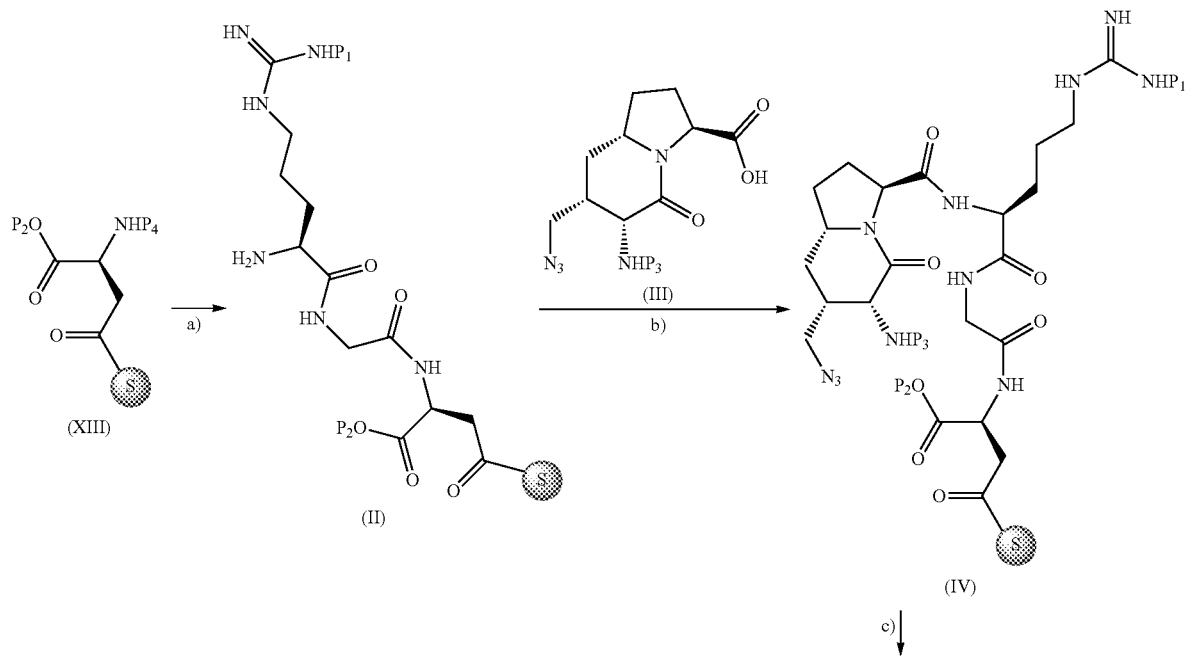
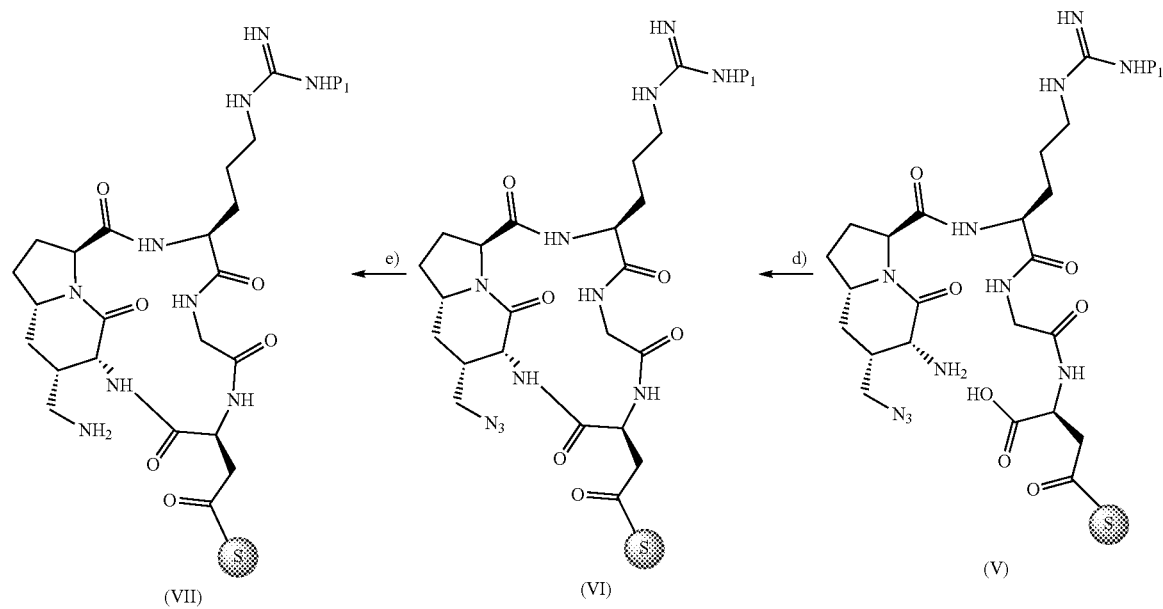

Scheme 3a
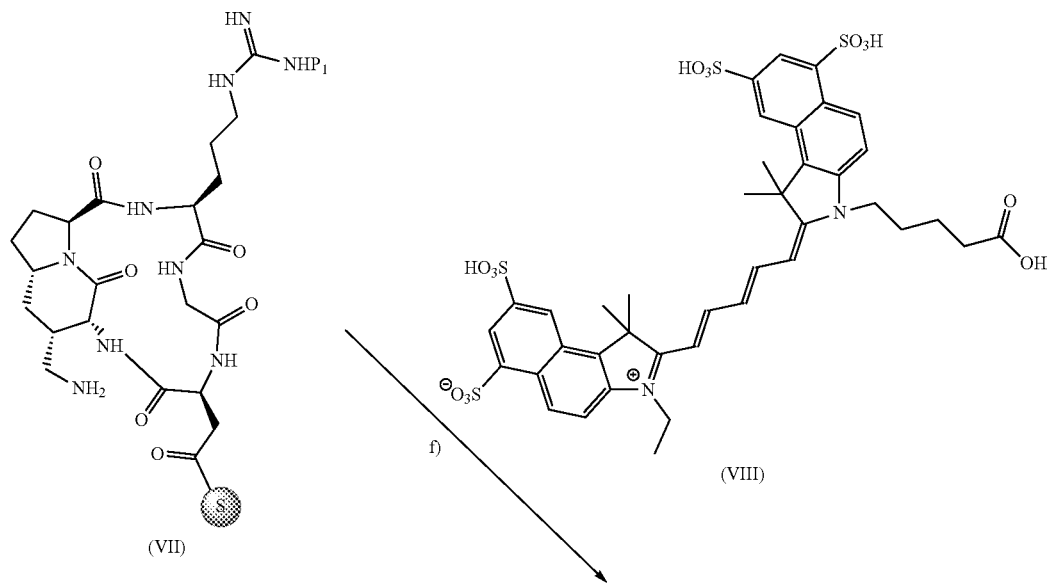
(VII)   f)   (VIII)
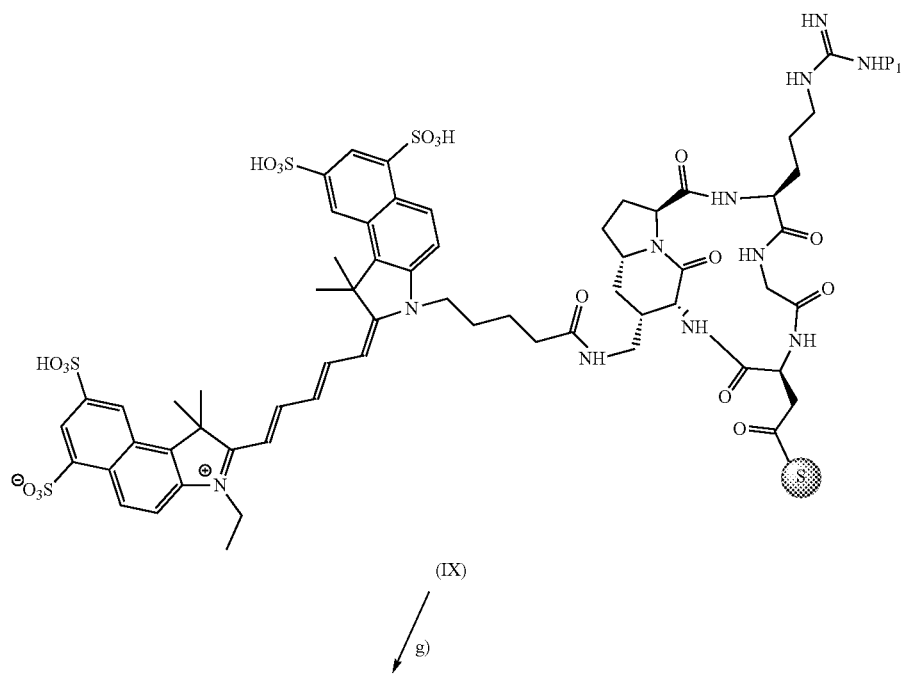
(IX)
g)

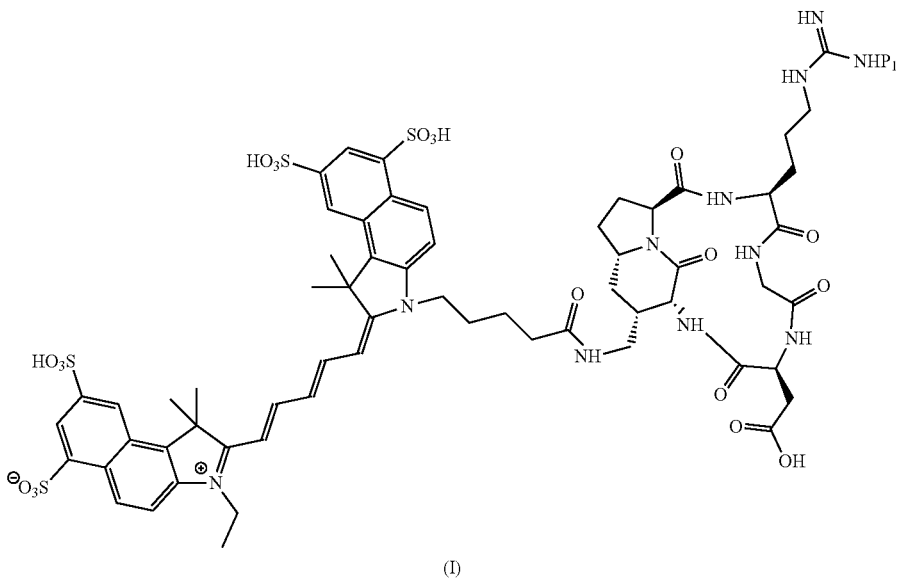

(I)

In Schemes 3 and 3a, the group S represents the solid support (resin) to which the amino acids are attached, and $P_1$, $P_2$, $P_3$ and $P_4$ are suitable protecting groups. In another embodiment of the present invention, the above described process further comprises the following steps:

h) purification of the compound of formula (I) obtained in step g), and optionally
i) lyophilization of the final product.

In a preferred embodiment of the present invention, $P_1$ is a sulfonyl or carbonyl protecting group.

Preferably, $P_1$ is selected from the group consisting of 2,2,4,6,7-pentamethyl-2,3-dihydro-1-benzofuran-5-sulfonyl (Pbf), o-nitrobenzenesulfonyl (oNBS), 2,4-dinitrobenzenesulfonyl (dNBS), benzothiazole-2-sulfonyl (Bts), 2,2,5,7,8-pentamethylchroman-6-sulfonyl (Pmc) 2,3,6-trimethyl-4-methoxybenzene-sulfonyl (Mtr), p-toluenesulfonyl (Tos) and tert-butyloxycarbonyl (Boc); particularly preferred being 2,2,4,6,7-pentamethyl-2,3-dihydro-1-benzofuran-5-sulfonyl (Pbf). In another preferred embodiment of the present invention, $P_2$ is a protecting group represented by benzyl or alkyl groups.

Preferably, $P_2$ is selected from the group consisting of allyl, alkyl, t-butyl, trityl (Trt), 2,4-dimethoxybenzyl (DMB), benzyl (Bn), 9-fluorenylmethyl (Fm), 2-chlorotrityl (2-Cl-Trt), 2-phenylisopropyl (2-PhiPr), 5-phenyl-3,4-ethylenedioxythenyl derivatives (Phenyl-EDOTn), 4-(N-[1-(4,4-dimethyl-2,6-dioxocyclohexylidene)-3-methylbutyl]-amino)benzyl (Dmab), carbamoylmethyl (Cam), p-nitrobenzyl (pNB), 2-trimethylsilylethyl (TMSE), (2-phenyl-2-trimethylsilyl)ethyl (PTMSE), 2-(trimethylsilyl)isopropyl (Tmsi), 2,2,2-trichloroethyl (Tce), p-hydroxyphenacyl, 4,5-dimethoxy-2-nitrobenzyl (Dmnb), 1,1-dimethylallyl (Dma), pentaamine cobalt (III), β-menthyl (Men), β-3-methylpent-3-yl (Mpe), 4-(3,6,9-trioxadecyl) oxybenzyl (TEGBz or TEGBn); particularly preferred being allyl.

In another preferred embodiment of the present invention, $P_3$ is a protecting group represented by carbonyl or acetyl groups.

Preferably, $P_3$ is selected from the group consisting of allyloxycarbonyl (Alloc), benzyloxycarbonyl (Cbz), 2-(4-biphenyl)isopropyloxycarbonyl (Bpoc), 3,5-dimethoxyphenylisopropyloxycarbonyl (Ddz), 2-(4-nitrophenylsulfonyl) ethoxycarbonyl (Nsc), 1,1-dioxobenzo[b]thiophene-2-ylmethyloxycarbonyl (Bsmoc), (1,1-dioxonaphtho[1,2-b] thiophene-2-yl)methyloxycarbonyl (α-Nsmoc), 1-(4,4-dimethyl-2,6-dioxocyclohex-1-ylidene)-3-methylbutyl (ivDde), tetrachlorophthaloyl (TCP), 2-phenyl(methyl)sulfonio)ethyloxycarbonyltetrafluoroborate (Pms), ethanesulfonylethoxycarbonyl (Esc), 2-(4-sulfophenylsulfonyl) ethoxycarbonyl (Sps), trichloroethyloxycarbonyl (Troc), p-nitrobenzyloxycarbonyl (pNZ), propargyloxycarbonyl (Poc), o-nitrobenzyloxycarbonyl (oNZ), 4-nitroveratryloxycarbonyl (NVOC), (2-nitrophenyl)propyloxycarbonyl (NPPOC), azidomethyloxycarbonyl (Azoc), trifluoroacetyl; particularly preferred being allyloxycarbonyl (Alloc).

The intermediate compound of formula (III), wherein $P_3$ is a suitable protecting group, as defined above, is a further object of the present invention.

The preparation of the intermediate of formula (III) is described in Scheme 4:

Scheme 4

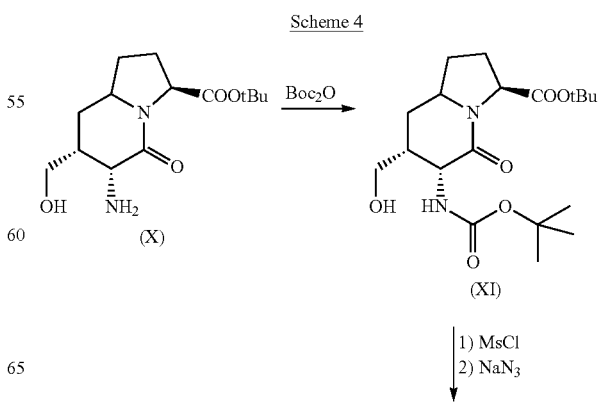

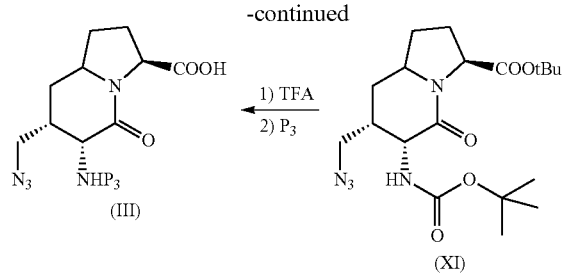

(III)     1) TFA    2) P₃     (XI)

Definitions

In the present description, and unless otherwise provided, the following terms are intended to have the following meanings.

The term "coupling reagent" refers to a reagent used in the formation of an amide bond between a carboxyl moiety and an amino moiety. The reaction may consist of two consecutive steps: activation of the carboxyl moiety and then acylation of the amino group. Coupling reagents are well known in the art, as described for instance in A. El-Faham and F. Albericio Chem. Rev. 2011, 111, 6557-6602; E. Valeur and M. Bradley Chem. Soc. Rev. 2009, 38, 606-631. Coupling reagents of the present invention typically include at least a functionality selected from phosphonium, aminium, imonium and imide group, which are able to react with the respective carboxyl group to give an activated intermediate. Non limiting examples of coupling agents are selected from the group consisting of: carbodiimides, such as N,N'-Diisopropylcarbodiimide (DIC), N,N'-dicyclohexylcarbodiimide (DCC), 1-ethyl-3-(3-dimethylaminopropyl) carbodiimide (EDAC), 1-ethyl-3-(3-dimethylaminopropyl) carbodiimide (EDC) and 1-ethyl-3-(3-dimethylaminopropyl)carbodiimide (WSC); phosphonium reagents, such as (benzotriazol-1-yloxy)tris(dimethylamino)phosphonium hexafluorophosphate (BOP), (benzotriazol-1-yloxy)tripyrrolidinophosphonium hexafluorophosphate (PyBOP), 7-Azabenzotriazol-1-yloxy-tripyrrolidino-phosphonium hexafluorophosphate (PyAOP), [Ethyl cyano(hydroxyimino)acetato-02]tri-1-pyrrolidinylphosphonium hexafluorophosphate (PyOxim), Bromotripyrrolidinophosphonium hexafluorophosphate (PyBrOP) and 3-(Diethoxyphosphoryloxy)-1,2,3-benzotriazin-4(3H)-one (DEPBT); and aminium/Uronium-Imonium reagents, such as N,N,N',N'-tetramethyl-O-(benzotriazol-1-yl)uronium tetrafluoroborate (TBTU), N,N,N',N'-tetramethyl-O-(1H-benzotriazol-1-yl) uronium hexafluorophosphate (HBTU), N,N,N',N'-tetramethyl-O-(7-azabenzotriazol-1-yl)uronium hexafluorophosphate (HATU), O-(1H-6-Chlorobenzotriazole-1-yl)-1,1,3,3-tetramethyluronium hexafluorophosphate (HCTU), 1-[1-(cyano-2-ethoxy-2-oxoethylidene-aminooxy)-dimethylamino-morpholino]-uronium hexafluorophosphate (COMU) and Fluoro-N,N,N',N'-tetramethylformamidinium hexafluorophosphate (TFFH).

Preferred coupling reagents of the present invention are PyAOP, HATU and COMU. The term "protecting group" designates a group adapted to preserving the function to which it is bound. Specifically, protective groups are used to preserve amino or carboxyl functions. Appropriate protecting groups are represented for instance by benzyl, carbonyl, alkyl, sulfonyl and acetyl groups which are well known to those skilled in the art and are described in conventional manuals, such as T. W. Green, Protective Groups in Organic Synthesis, 4th Edition (Wiley, N.Y. 2007). Examples of suitable protecting groups include, but are not limited to, formyl, trifluoroacetyl, acetyl, 9-fluoromethyloxycarbonyl (Fmoc), benzyloxycarbonyl (Cbz), t-butoxycarbonyl (Boc), isopropyloxycarbonyl, allyl, allyloxycarbonyl (Alloc), benzyl and triphenylmethyl. Among these moieties, the Fmoc is a preferred protecting group.

The amino acids side-chains can be blocked with protecting groups (removable by hydrogenation, acid or basic treatments or other conditions), selected from the group consisting of 2,2,4,6,7-pentamethyl-2,3-dihydro-1-benzofuran-5-sulfonyl (Pbf), o-nitrobenzenesulfonyl (oNBS), 2,4-dinitrobenzenesulfonyl (dNBS), benzothiazole-2-sulfonyl (Bts), 2,2,5,7,8-pentamethylchroman-6-sulfonyl (Pmc) 2,3,6-trimethyl-4-methoxybenzene-sulfonyl (Mtr), p-toluenesulfonyl (Tos), and tert-butyloxycarbonyl (Boc), allyl, alkyl, t-butyl, trityl (Trt), 2,4-dimethoxybenzyl (DMB), benzyl (Bn), 9-fluorenylmethyl (Fm), 2-chlorotrityl (2-Cl-Trt), 2-phenylisopropyl (2-PhiPr), 5-phenyl-3,4-ethylenedioxythenyl derivatives (Phenyl-EDOTn), 4-(N-[1-(4,4-dimethyl-2,6-dioxocyclohexylidene)-3-methylbutyl]-amino) benzyl (Dmab), carbamoylmethyl (Cam), p-nitrobenzyl (pNB), 2-trimethylsilylethyl (TMSE), (2-phenyl-2-trimethylsilyl)ethyl (PTMSE), 2-(trimethylsilyl)isopropyl (Tmsi), 2,2,2-trichloroethyl (Tce), p-hydroxyphenacyl, 4,5-dimethoxy-2-nitrobenzyl (Dmnb), 1,1-dimethylallyl (Dma), pentaamine cobalt (III), β-menthyl (Men), β-3-methylpent-3-yl (Mpe), 4-(3,6,9-trioxadecyl)oxybenzyl (TEGBz or TEGBn), allyloxycarbonyl (Alloc), benzyloxycarbonyl (Cbz), 2-(4-biphenyl)isopropyloxycarbonyl (Bpoc), 3,5-dimethoxyphenylisopropyloxycarbonyl (Ddz), 2-(4-nitrophenylsulfonyl) ethoxycarbonyl (Nsc), 1,1-dioxobenzo[b]thiophene-2-ylmethyloxycarbonyl (Bsmoc), (1,1-dioxonaphtho[1,2-b] thiophene-2-yl)methyloxycarbonyl (α-Nsmoc), 1-(4,4-dimethyl-2,6-dioxocyclohex-1-ylidene)-3-methylbutyl (ivDde), tetrachlorophthaloyl (TCP), 2-phenyl(methyl)sulfonio)ethyloxycarbonyltetrafluoroborate (Pms), ethanesulfonylethoxycarbonyl (Esc), 2-(4-sulfophenylsulfonyl) ethoxycarbonyl (Sps), trichloroethyloxycarbonyl (Troc), p-nitrobenzyloxycarbonyl (pNZ), propargyloxycarbonyl (Poc), o-nitrobenzyloxycarbonyl (oNZ), 4-nitroveratryloxycarbonyl (NVOC), (2-nitrophenyl)propyloxycarbonyl (NPPOC), azidomethyloxycarbonyl (Azoc) and trifluoroacetyl.

The expression "acid/scavenger cocktail" includes within its meaning a cleavage acid reagents mixture suitable for removing some protecting groups, particularly Mtr (2,3,6-trimethyl-4-methoxybenzene-sulfonyl), Pmc (2,2,5,7,8-pentamethyl-6-chromane-sulfonyl), OtBu (tert-butyl ester), Trt (triphenylmethyl), Pbf (2,2,4,6,7-pentamethyl-2,3-dihydro-1-benzofuran-5-sulfonyl) and BOC (tert-butoxycarbonyl). Preferably, the acid/scavenger cocktails can comprise TFA, triisopropylsilane (TIS), 1,2-ethanedithiol (EDT), phenol, water, anisole, thioanisole, 1-dodecanethiol, methanesulfonic acid, triethylsilane, indole, dichloromethane, dithiotreitol or mixtures thereof.

Detailed Description

As said above, the method herein described has the advantage of quickly and efficiently providing the final compound of formula (I) in few steps.

In fact, the only preparation performed in solution phase is represented by the synthesis of the aza-bicycloalkane intermediate of formula (III), which is obtained according to the method described in Scheme 4. The rest of the synthesis is performed on solid support, as herewith described in detail.

Synthesis on Solid Support

According to the present invention, the choice to perform the synthesis on solid-support has required redefining the chemistry and the reactions strategy, in particular with respect to the selection of the protecting groups.

The synthesis steps described in Scheme 3 may typically be performed continuously on a peptide synthesizer essentially without human intervention once synthesis is started, apart from control sampling for reactions monitoring.

Delivery of reagents and solvents is preferably automated, either to cartridges for amino acids activation or to reaction vessels. Considering the latter one, delivery is realized for either allowing reaction to be performed on solid support or for washing the solid support. Moreover, chemicals reactions can be done for different batches on separate reaction vessels.

Typical reactions are removal of a protecting group or coupling of two reactive moieties.

Synthesis is preferably executed under inert conditions, wherein air is removed and substituted by an inert gas such as argon or nitrogen; however most of the reaction steps can also be performed under atmosphere conditions.

The relevant solid-phase synthetic techniques well known in the art, such as those described for instance in Merrifield et al., *J. Am. Chem. Soc.* 1963, 85, 2149; Barany et al., *Int. J. Peptide Protein Res.* 1987, 30(6), 705-739 and Coin et al., *Nature Protocols* 2007, 2, 3247-3256 have been considered for the present synthesis and incorporated herein by reference. In particular, the known Fmoc solid-phase peptide synthesis (SPPS) protocol, using the base-labile 9-fluoromethyloxycarbonyl (Fmoc) group as the protecting alpha-amino group, is preferably applied in the present invention.

Resins

According to the present invention, different resins can be used as solid support for the synthesis of DA364. The resins most frequently used in the art can include, but are not limited to, hydroxymethyl resin, Wang resin, 2-chlorotrityl resin, Rink amide resin (specific for Fmoc SPPS); Merrifield resin, 4-methylbenzhydrylamide (MBHA) resin, oxime resin (specific for Boc SPPS). These resins are commercially available and have been extensively used in solid-phase synthesis of peptides.

In a preferred embodiment of the present invention the synthesis of DA364 is performed using a p-benzyloxybenzyl alcohol (Wang) resin, suitable for amino acids having a free carboxyl group. More preferably, a commercial Fmoc-Asp (Wang resin)-OAll resin is used, which is particularly useful for the synthesis of cyclic peptides. The on-resin cyclization is the simplest approach for the preparation of head-to-tail cyclic peptides. The strategy involves anchoring to a solid phase an Asp or Glu residue bearing orthogonal α-carboxyl protection via the side chain β (herein Allyl group), as described for instance in Delforge et al., *Letters in Peptide Science* 1996, 3, 89-97; S. A. Kates, et al., *Tetrahedron Lett.* 1993, 34, 1549; A. Trzeciak & W. Bannwarth, *Tetrahedron Lett.* 1992, 33, 4557; C. Flouzat, et al., *Tetrahedron Lett.* 1997, 38, 1191. This resin can be suitably chosen as it bears the protected amino acid residue (Asp), which is the C-terminus amino acid of the tripeptide RGD, directly linked to the Wang resin. The linear peptide is assembled on the alpha-amino group of the Asp residue. The orthogonal carboxyl protecting group (-allyl) is then removed and a lactam bridge is formed between the N-terminal amine and C-terminal carboxyl group, before cleavage of the desired cyclic peptide from the solid phase.

The solid supports are used on an automated peptide synthesizer and can be conveniently treated with suitable solvents such as N,N-dimethylformamide (DMF), dimethylacetamide (DMA), methylene chloride (DCM), tetrahydrofuran (THF), N-methylmorpholine, collidine hexafluoroisopropanol (HFIP), trifluoroethanol (TFE), preferably with DMF, before use. For instance, Fmoc-Asp(Wang resin)-OAll resin is preferably conditioned/covered with DMF and allowed to swell for a period comprised between 1 minute and 4 hours.

The loading capacity of Fmoc-Asp(Wang resin)-OAll resin is generally comprised from 0 to 10 mmol/g. In a preferred embodiment of the present invention the loading of the resin is 0.2 to 4.0 mmol/g; more preferably, the loading is 0.3 mmol/g.

Amino Acid Protecting Groups

According to the present invention, the alpha-amino group used in the peptide elongation can be protected during the amino acid coupling with suitable protecting groups well known in the art. For instance, suitable protecting groups are defined above. However, the Fmoc is the preferred protecting group.

Furthermore, some individual amino acids may have the side-chains blocked with protecting groups during the reactions and as long as the compound is attached to the resin. These protecting groups should preferably be stable under the reaction conditions at each step of the synthesis. In fact, it can be advantageous to remove them at the same time as the final compound is cleaved from the resin. In this respect, they can be for instance distinguished depending on whether they are removable by acid or basic treatment. Examples of these protecting groups are defined above.

According to the present invention, the amino acid arginine (Arg) can be preferably protected with an acid-labile protecting group. More preferably, the protecting group Pbf is used.

Synthesis of the Azabicycloalkane-cRGD on the Resin (Steps a-e)

The first Step a) of the present invention involves attachment to the resin and addition of the amino acids to form the tripeptidic chain RGD (II) by a process comprising the steps of:
  i—deprotection of the alpha-amino protecting group with a deprotecting agent;
  ii—coupling of the amino acid with a coupling reagent in an organic solvent; and
  iii—capping of the remaining amines.

A washing step with a suitable washing solution is performed after each deprotecting and coupling step. Typically the washing solution is represented by a polar aprotic solvent, such as tetrahydrofuran (THF), methylene chloride (DCM), N-methylpyrrolidone (NMP), N,N-dimethylformamide (DMF) and N,N-dimethylacetamide (DMA), or water or buffer.

According to the present invention, the primary solvents used for deprotection, coupling and washing include, but are not limited to, DCM, DMF and THF.

Deprotection is the action of removing the alpha-amino protecting groups, and particularly Fmoc, in order to allow the coupling of the next amino acid. According to the present invention, the deprotecting agent for Fmoc protecting group can be a solution of 20% of piperidine in DMF.

After deprotection of the alpha-amino group, the subsequent amino acid (Gly and Arg) is added in sequence to produce the desired tripeptide.

The coupling steps leads to the formation of an amide bond between the amino acid residues and are performed in the presence of a coupling reagent and some additives enhancing the reactivity of the intermediates.

According to the present invention, the coupling reagent can be selected from the reagents commonly used for peptide bond formation, for instance selected among the groups reported above.

Preferred coupling reagents of the present invention are PyAOP, HATU and COMU. Some additives can be also used in the coupling reaction in order to make process faster and cleaner. Examples of such additives are represented for instance by HOBt, HOAt, EDC, BOP, OxymaPure, DIC and DCC. Among the above compounds, HOBt, HOAt and OxymaPure are preferred embodiments Accordingly, in a preferred embodiment of the present invention couplings are performed by adding the activated amino acid with DIC as coupling reagent and OximaPure as additive, for a period of from 1 to 6 hours, preferably for 4 hours.

At the end of coupling, a capping step is performed in order to close up any remaining amine. This step is preferably performed by adding a solution of acetic anhydride in DMF. The ratio between anhydride acetic solution and the active capacity of the resin can be from 1:1 to 1:300 (mol/mol); preferably it is about 1:150.

At the last stage of the RGD synthesis, the Fmoc of Arg is removed, but no capping is performed and the obtained intermediate of formula (II) can be subsequently used without further purification.

According to Step b), the RGD peptide linked to the solid support (II) is coupled to the aza-bicycloalkane of formula (III), prepared according to the procedure reported in Scheme 4. The intermediate (III) is obtained in four steps starting from (3R,4R,6S,9S)-3-benzylamino-1-aza-2-oxo-4-hydroxy-methylbicyclo[4.3.0]nonane-carboxylic acid tert-butyl ester, whose synthesis is described in Manzoni et al., $J.$ $Org.$ $Chem.$ 2005, 70(10), 4124-4132 (compound 25). This compound (X) is firstly protected on the amino group with tert-butoxycarbonyl (Boc) to obtain compound (XI), which is activated with MsCl and TEA and then undergoes a substitution with $NaN_3$ in DMF, providing compound (XII). The latter is deprotected on the carboxylic function with TFA and then reacted with a suitable protecting group $P_3$ to give the aza-bicycloalkane of formula (III).

The coupling reaction according to step b) is anticipated by the activation of the aza-bicycloalkane (III), which is performed in the presence of a coupling reagent, selected from those described above, and a base.

Preferably the coupling reagent is selected among the aminium/uranium-imonium reagents and the base is a tertiary amine. More preferably, the coupling reagent is COMU and the base is N,N-Diisopropylethylamine.

The ratio between the intermediate compound (II) and the coupling reagent can be comprised between 1:1 and 1:5 (mol/mol). Preferably, the ratio is comprised between 1:1.5 and 1:3 and more preferably it is about 1:2 (mol/mol).

The ratio between the aza-bicycloalkane compound (III) and the coupling reagent can be from 1:0.95 to 1:0.99 (mol/mol), preferably it is about 1:0.98 (mol/mol).

The ratio between the aza-bicycloalkane compound (III) and the N,N-diisopropylethylamine can be from 1:2 to 1:5 (mol/mol), preferably it is about 1:2 (mol/mol).

The activation phase of the compound (III) can last from 1 to 10 minutes, preferably it lasts 3 minutes. The subsequent coupling phase of the compound (III) with compound (II) to provide the peptidomimetic compound of formula (IV) can last from 1 to 20 hours.

According to a preferred embodiment of the present invention, at the end of the reaction the medium is filtered, and washed (e.g. with DMF).

The resultant compound of formula (IV) undergoes then deprotection according to Step c). Preferably the protecting groups used for this compound are respectively an allyl group at the carboxyl function and an allyloxycarbonyl (Alloc) group at the amino moiety of the aza-bicycloalkane. An example of removal of the Allyl/Alloc protecting groups is described for instance in Grieco P. et al., $J.$ $Peptide$ $Res.,$ 2001, 57, 250-256. Automated deprotection of allyloxycarbonyl and allyl functions on intermediate of formula (IV) to provide the intermediate of formula (V) is performed under Argon atmosphere with a prior activation phase of about 3 minutes wherein an organosilane, such as a phenylsilane, is added, followed by the addition of a metal catalyst, such as a palladium catalyst, dissolved in a suitable solvent such as DCM, previously purged with Argon. Preferably, the organosilane is $PhSiH_3$ and the catalyst is tetrakis(triphenylphosphine)palladium (0) ($Pd(PPH_3)_4$).

The ratio between the intermediate (IV) and the phenylsilane can be from 1:10 to 1:50 (mol/mol); preferably it is about 1:25 (mol/mol).

The deprotection is preferably performed under stirring, for 30-60 min., preferably for 40 min.

The subsequent intramolecular cyclization on intermediate (V) to provide the intermediate (VI), referred to Step d), is carried out in the presence of a base and a coupling reagent, preferably a tertiary amine and an aminium/uranium-iminium reagent, more preferably N,N-diisopropylethylamine and PyAOP, during a period from 1 hour to 20 hours, preferably for 17 hours.

The ratio between the intermediate (V) and the aminium/uranium-iminium reagent can be from 1:1 to 1:5 (mol/mol); preferably it is about 1:1.5 (mol/mol).

The ratio between the intermediate (V) and the base can be from 1:1 to 1:5 (mol/mol); preferably it is about 1:3 (mol/mol).

The medium is then filtered and washed about 5 times with a suitable solvent, such as DMF.

Step e) involves the reduction of the azido-derivative (VI) to the corresponding amino-derivative (VII). An example of this type of reaction, namely the Staudinger reaction involving azides reacting with phosphanes, is described in Quan Tian W. et al, $J.$ $Org.$ $Chem.$ 2004, 69, 4299-4308.

The reduction step can be performed between 20° C. and 70° C., preferably at 60° C., in the presence of an organophosphorous compound, such as triphenylphosphine, and water for a period from 5 hour to 20 hours, preferably for 17 hours.

The ratio between the intermediate (VI) and triphenylphosphine can be from 1:1 to 1:20 (mol/mol); preferably it is about 1:10 (mol/mol).

The ratio between the intermediate (VI) and water can be from 1:20 to 1:100 (mol/mol); preferably it is about 1:50 (mol/mol).

At the end of the reaction the resin is preferably washed, e.g. three times with 1% $Et_3N$ in DCM and two times with $Et_2O$.

Conjugation of the Fluorophore to the Azabicycloalkane-cRGD-Resin

Step f) involves the conjugation of the peptidomimetic of formula (VII) with the fluorophore Cy5.5 of formula (VIII).

The compound (VIII) needs to be activated, for instance from 1 to 10 min with a base and a coupling reagent, before coupling to intermediate (VII) leading to compound (IX). Preferably, the activation is carried out with a tertiary amine and an aminium/uronium-imonium reagent for 3 minutes, and the period of the coupling can be from 1 to 24 hours.

More preferably, the activation is carried out with N,N-diisopropylethylamine and COMU, and the coupling lasts about 20 hours.

The ratio between compound (VIII) and the coupling reagent can be from 1:0.95 to 1:0.99 (mol/mol); preferably it is about 1:0.98 (mol/mol). The ratio between compound (VIII) and the N,N-diisopropylethylamine can be from 1:2 to 1:5 (mol/mol), preferably about 1:2 (mol/mol). At the end, resin is filtered and about 5 washings with a suitable solvent such as DMF are carried out.

Cleavage of Compound (I) from the Resin and Deprotection

The final peptidomimetic compound (I) is recovered as crude product according to Step g).

The deprotection of the guanidinium group on the arginine residue in compound (IX) and the simultaneous cleavage of the final product from the resin, generating the carboxylic group of the aspartic acid residue, may be carried out according to well-known techniques (for instance described in Sole, N. A. et al., *J. Org. Chem.* 1992, 57, 5399-5403; Huang, H. et al., *J. Peptide Res.* 1999, 53, 548-553; King, D. et al., *Int. J. Peptide Protein Res.* 1990, 36, 255-266; Bonner, A. G. et al., *J. Peptide Res.* 2001, 57, 48-58; Albericio, F. et al., *J. Org. Chem.* 1990, 55, 3730-3743), with efficient acid/scavenger cocktails, such as for instance TFA/triisopropylsilane(TIS)/$H_2O$, to obtain the compound of formula (I). The ratio between TFA, TIS and water can be from 80/10/10 to 95/2.5/2.5; preferably it is 95/2.5/2.5.

The deprotection can be performed under stirring, at room temperature and in the dark from 1 hour to 8 hours, preferably for 3 hours. The reaction mixture is then filtered and the blue solution can be washed with diethyl ether.

Purification of the Final Crude Compound of Formula (I)

Final crude product (I) is finally recovered after precipitation and purified with preparative HPLC system according to Step h). Pooled fractions of the isolated compound can be then optionally lyophilized according to Step i).

Preparative HPLC can be performed with a preparative column having stationary phase dedicated for reverse phase HPLC, with appropriate mobile phase for eluting compounds of interest in a pure fraction. HPLC is used to separate and refine high-purity target compounds from the crude solution after a cleavage of peptidomimetic residue from solid support.

For instance, preparative reversed phase HPLC can conveniently be performed on a AKTA PURE 25 system with a RP-HPLC Luna Phenomenex $C_{18}$ preparative column (250×10 mm). Purification can be performed by eluting with a linear gradient from 0 to 95% acetonitrile with 0.1% of TFA.

As described above, the allocated time for purifications in the overall synthesis is considerably reduced, as only one step of purification remains at the final stage to collect the pure product.

The invention and its particular embodiments described in the following part are only exemplary and not to be regarded as a limitation of the present invention: they show how the present invention can be carried out and are meant to be illustrative without limiting the scope of the invention.

EXPERIMENTAL PART

Materials and Equipment

All commercially available reagents employed in the synthesis of DA364 were used without further purification.

Analytical reversed phase HPLC was performed on a SHIMADZU UFLC system consisting of a SHIMADZU UFLC binary solvent manager, a SHIMADZU UFLC controller (CBM-20A) and a SHIMADZU HPLC UV-VIS detector (SPD-20A) equipped with a RP-HPLC Luna Phenomenex $C_{18}$ analytical column (250×4.6 mm). Analyses were performed using either a linear gradient of phase A (10 mM $AcONH_4$ in $H_2O$) and phase B (10 mM $AcONH_4$ in $ACN/H_2O$ 9/1) or a linear gradient of phase A (0.1% TFA in $H_2O$) and phase B (0.1% TFA in ACN) at 1.0 mL/min with UV detection at 214 nm. 20 µL were injected and column temperature was not controlled.

Preparative reversed phase HPLC was performed on an AKTA PURE 25 system equipped with a RP-HPLC Luna Phenomenex $C_{18}$ preparative column (250×10 mm). Purification was performed by eluting with a linear gradient from 0 to 95% acetonitrile with 0.1% of TFA.

Mass spectrometry was performed on Agilent 1100 LC/MSD instrument.

A TRIBUTE peptide synthesizer from Gyros Protein Technologies was used for the solid phase synthesis.

The abbreviations for individual amino acids residues are conventional: Asp or D is aspartic acid, Gly or G is glycine, Arg or R is arginine. The amino acids herein referred to should be understood to be of the L-isomer configuration unless otherwise noted.

List of Abbreviations
Alloc Allyloxycarbonyl
API Active Pharmaceutical Ingredient
BOP (Benzotriazol-1-yloxy)tris(dimethylamino)phosphonium hexafluorophosphate
COMU (1-Cyano-2-ethoxy-2-oxoethylidenaminooxy)dimethylamino morpholino-carbenium hexafluorophosphate
Cy5.5 Sulfo-Cyanine5.5 carboxylic acid
DCC N,N'-dicyclohexylcarbodiimide
DCM Dichloromethane
DEPBT 3-(Diethoxyphosphoryloxy)-1,2,3-benzotriazin-4(3H)-one
DIC N,N'-Diisopropylcarbodiimide
DIPEA or DIEA N,N-Diisopropylethylamine
DMA Dimethylacetamide
DMF Dimethylformamide
EDAC 1-ethyl-3-(3-dimethylaminopropyl)carbodiimide
EDC 1-ethyl-3-(3-dimethylaminopropyl)carbodiimide
Eq. Equivalent
$Et_3N$ Triethylamine
$Et_2O$ Diethyl ether
Fmoc Fluorenylmethoxycarbonyle
HATU (1-[Bis(dimethylamino)methylene]-1H-1,2,3-triazolo[4,5-b] pyridinium 3 oxide hexafluorophosphate)
HBTU N,N,N',N'-Tetramethyl-O-(1H-benzotriazol-1-yl) uronium hexafluorophosphate
$H_2O$ Water
HOAt 1-Hydroxy-7-azabenzotriazole
HOBt Hydroxybenzotriazole
HPLC High-performance liquid chromatography
NMP N-Methyl-2-pyrrolidone
OAll Allyl ester
OxymaPure Ethyl cyano(hydroxyimino)acetate
Pbf 2,2,4,6,7-Pentamethyldihydrobenzofuran-5-sulfonyl
$Pd(PPh_3)_4$ Tetrakis(triphenylphosphine)palladium(0)
$PhSiH_3$ Phenylsilane
$PPh_3$ Triphenylphosphine
PyAOP 7-Azabenzotriazol-1-yloxy-tripyrrolidino-phosphonium hexafluorophosphate
PyBOP benzotriazol-1-yl-oxytripyrrolidinophosphonium hexafluorophosphate
PyOxim [Ethyl cyano(hydroxyimino)acetato-02]tri-1-pyrrolidinylphosphonium hexafluorophosphate PyBrOP Bromotripyrrolidinophosphonium hexafluorophosphate
TBTU N,N,N',N'-Tetramethyl-O-(benzotriazol-1-yl)uronium tetrafluoroborate
TFA Trifluoroacetic acid
TFFH Fluoro-N,N,N',N'-tetramethylformamidinium hexafluorophosphate
THF Tetrahydrofuran
TIS Triisopropylsilane Example 1: Synthesis of Compound of Formula (I)

The synthesis of compound of formula (I) is performed according to the steps reported in Scheme 3. The reactions progress was followed using colorimetric test (TNBS) and UV monitoring at 301 nm of the dibenzofulvene-piperidine adduct, removed after each Fmoc-deprotection steps.

Step a) Tripeptide RGD Synthesis

Peptide synthesis was carried out by standard Fmoc-Solid Phase Strategy using a Fmoc-Asp(Wang resin)-OAll as solid support (1000 mg, loading capacity: 0.469 mmol/g, active capacity: 0.469 mmol). A reactor of 40 mL was used. Resin was covered with 10 mL of DMF and allowed to swell for 10 min. This operation was repeated 3 more times. Already loaded amino acid (Fmoc-Asp-OAll) was Fmoc deprotected with 10 mL of a 20% (v/v) piperidine in DMF for 30 sec. Next, Fmoc-Gly-OH was activated with 8 mL of a DIC/OxymaPure solution for 10 min before being added on the previous Fmoc deprotected amino acid attached to the solid support. After each coupling, in order to block unreacted free amino groups, a capping with 8 mL of anhydride acetic (150 eq.) was performed for 5 min.

Then, Fmoc-Gly-OH recently added on the growing structure was Fmoc deprotected with 10 mL of a 20% (v/v) piperidine in DMF for 30 sec. After, Fmoc-Arg(Pbf)-OH was activated with 8 mL of a DIC/OxymaPure solution for 10 min before being added on the previous Gly. Then, a capping with 8 mL of acetic anhydride (150 eq.) was performed for 5 min. Last residue was Fmoc deprotected with 10 mL of a 20% (v/v) piperidine in DMF for 30 sec. Lastly, coupling product on resin was washed with 8 mL of MeOH, 3 times for 30 sec. The obtained intermediate (II) was then used without further purification.

Step b) Coupling of Aza-Bicycloalkane with RGD

The intermediate compound (III) was synthesized according to the procedures described above in Scheme 4 and in the Example 2.

The intermediate (II) was swelled in DCM. Then, in another flask the intermediate (III) (38.5 µmol) was activated for 3 min. with HATU (37.7 µmol) and DIPEA (77.0 µmol) before being added to the mixture comprising intermediate (II) and agitated. The coupling reaction lasted 20 hours and the medium was then filtered. DMF (3 mL) was added and the medium was stirred for 30 sec. Then, DMF was filtered and the washing step was repeated 4 more times. The intermediate (IV) thus obtained was used without further purification.

Step c) Allyl-Alloc Deprotection

Before performing the reaction, the mounting system was inerted with nitrogen gas. The intermediate (IV) was then activated by adding $PhSiH_3$ (0.963 mmol) and let to react for 3 min. Afterwards, $Pd(PPh_3)_4$ (15.4 µmol) was added and deprotection lasted 40 min. After completion of the reaction, resin was washed four times with 4 mL of DCM for 30 sec, once with 4 mL of a solution of dioxane:$H_2O$ (9:1) for 1 min, once with 4 mL of DMF for 2 min and twice with 4 mL of DCM for 2 min. This whole process for the deprotection was repeated twice with a fresh solution of $Pd(PPh_3)_4$. The obtained intermediate (V) was then used without further purification.

Step d) Cyclization of the Aza-Bicicloalkane-RGD

The intermediate (V) was activated with PyAOP (57.8 µmol) and DIPEA (116 µmol) and the reaction medium was stirred for 17 hours. After completion of the coupling, the solution was filtered and 3 mL of DMF were added, stirring the medium for 30 sec. DMF was then filtered and this washing step was repeated four more times.

The obtained intermediate (VI) was then used without further purification.

Step e) Reduction of the Azide

The intermediate (VI) was swelled in THF. Then, it was reduced at 60° C. in THF by adding $PPh_3$ (385 µmol) and $H_2O$ (1.925 mmol) and agitating the medium during 17 hours. Upon completion of the reaction, the resin was washed three times with 5 mL of 1% $Et_3N$ in DCM for 2 min and twice with 5 mL of $Et_2O$ for 2 min.

The obtained intermediate (VII) was then used without further purification.

Step f) Labelling with Fluorophore Cy5.5

The intermediate (VIII) was activated with COMU (6.30 mg) and DIPEA (1.5 eq) during 3 min before being added to intermediate (VII) dissolved in DMF. The coupling reaction lasted 20 hours. At the end, resin was filtered and 3 mL of DMF were added, stirring the medium for 30 sec. Then, DMF was filtered and the washing step was repeated 4 more times.

Step g) Cleavage and Deprotection

A freshly prepared TFA/scavenger cocktail (2 mL of a solution of trifluoroacetic acid:triisopropylsilane:water 95:2.5:2.5) was added to the crude obtained in the previous step f) and the mixture was allowed to stir at room temperature for 3 h. The reaction mixture was then filtered and the blue solution was washed three times with 8 mL of diethyl ether. The crude final compound (I) was finally obtained.

Step h) Purification

Final crude of compound (I) was purified on RP-HPLC Luna Phenomenex $C_{18}$ preparative column (250×10 mm) by eluting with a linear gradient from 0 to 95% acetonitrile with 0.1% of TFA. The collected fractions were analyzed by analytical HPLC-UV and Mass Spectrometry. Fractions of interest were combined and acetonitrile was evaporated.

Step i) Lyophilization

The resulting solution was frozen in an isopropanol bath at −40° C. The product was then lyophilized for 12 hours and was recovered as a blue powder.

Example 2: Synthesis of a Compound of Formula (III) Wherein $P_3$ is Alloc

The synthesis of compound of formula (III) is performed according to the steps reported in Scheme 4.

Synthesis of Compound (XI)

$BOC_2O$ (2.34 g, 10 mmol) was added to a solution of compound (X) (1.9 g, 6.68 mmol) (Manzoni et al., *J. Org. Chem.* 2005, 70 (10), 4124-4132) in THF (20 mL). The mixture was stirred for 2 h then the solvent was evaporated and the crude product (2.6 g) was directly used in the following step. Yield quantitative.

Synthesis of Compound (XII)

Methanesulfonyl chloride (1.1 mL, 14.2 mmol) was slowly added to a solution of compound (XI) (2.57 g, 6.68 mmol) in dry $CH_2Cl_2$ (20 mL) at 0° C.; then $Et_3N$ (4 mL, 28.4 mmol) was added. The reaction mixture was stirred at 0° C. for additional 1 h, warmed up to room temperature and washed with $NH_4Cl$ (2×5 mL). The organic phase was separated and the solvent was removed under reduced pressure to yield the crude mesylate which was dissolved in DMF (20 mL) at room temperature. $NaN_3$ (5.4 g, 83.1 mmol) was added and the reaction mixture was heated at 60°

C. and stirred for 3 h. DMF was evaporated under vacuum and the crude product was washed with H₂O (15 mL) and extracted with EtOAc (15 mL). The organic phase was separated and the residue was purified by column chromatography (CH₂Cl₂/iPrOH=130/0.8) to obtain 1.6 g of compound (XII). Yield 58%.

Synthesis of Compound (III)

A solution of compound (XII) (1.6 g, 3.9 mmol) in trifluoroacetic acid (20 mL) was stirred at room temperature for 18 h. Trifluoroacetic acid was evaporated and the crude product was dissolved in dry THF (25 mL) under nitrogen atmosphere. Diallyl dicarbonate (0.87 g, 4.7 mmol) was added and the mixture was stirred at 55° C. for 24 h. The solvent was removed and the crude product was purified by column chromatography (CH₂Cl₂/MeOH/NH₃ 8/2/0.2→7/3/0.3) to give 1.03 g of compound (III). Yield 78%

The invention claimed is:

1. A process on solid support for the preparation of the cRGD-Cy5.5 conjugate of formula (I)

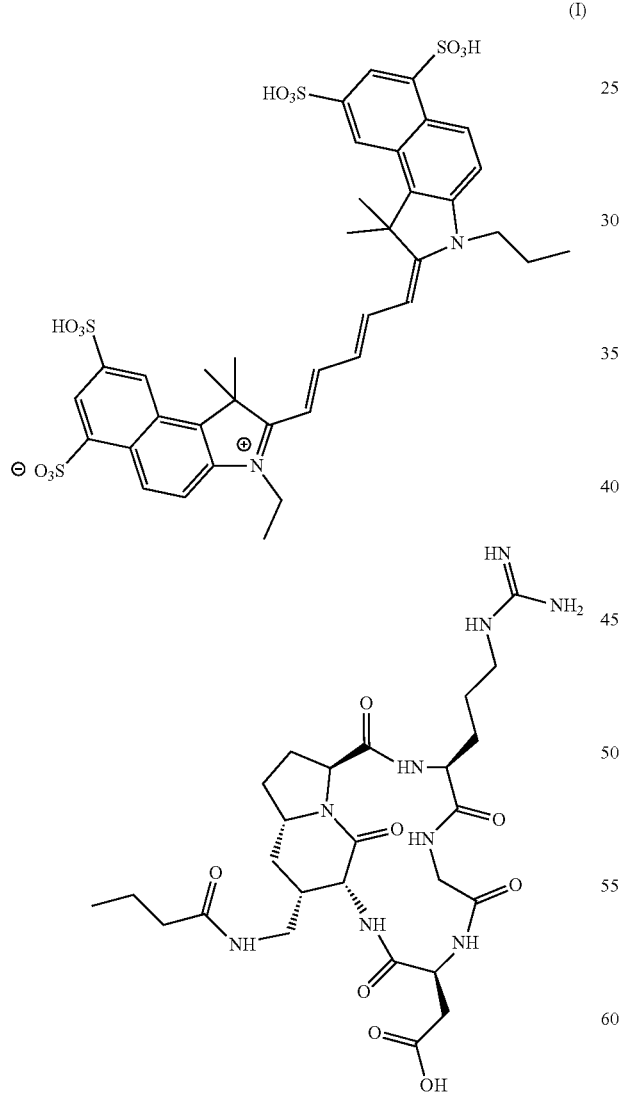

which comprises the steps of:
a) synthesising a tripeptide of formula (II) on a solid support

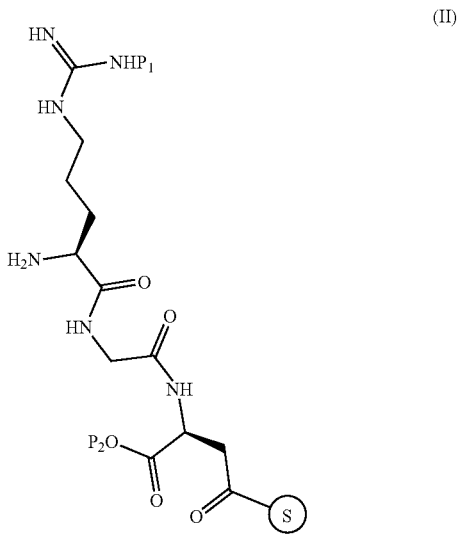

wherein P₁ and P₂ are protecting groups and S is the solid support;

b) coupling of the tripeptide of formula (II) linked to the solid support with an aza-bicycloalkane of formula (III)

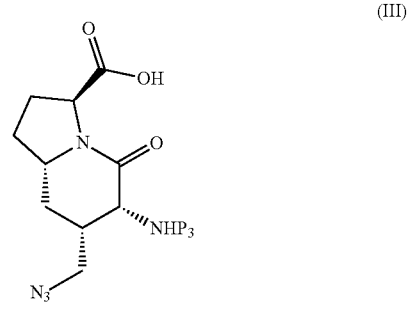

wherein P₃ is a protecting group, to provide a compound of formula (IV)

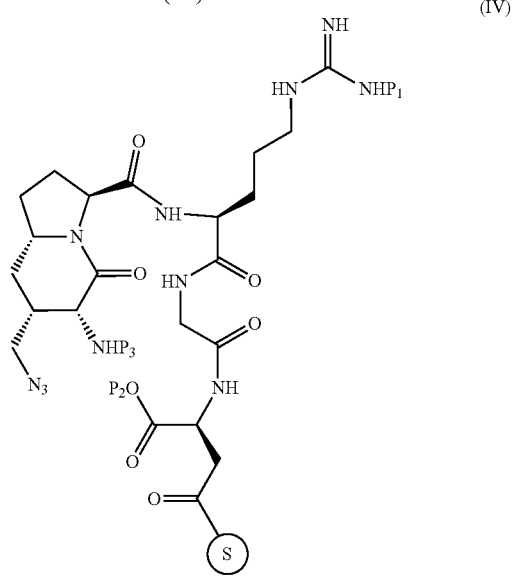

wherein P₁, P₂, P₃ and S are as defined above;

c) removing the protecting groups P₂ and P₃ from compound (IV) to provide a compound of formula (V)

e) subjecting the resulting compound of formula (VI) to a reduction reaction to provide a corresponding amino-derivative of formula (VII)

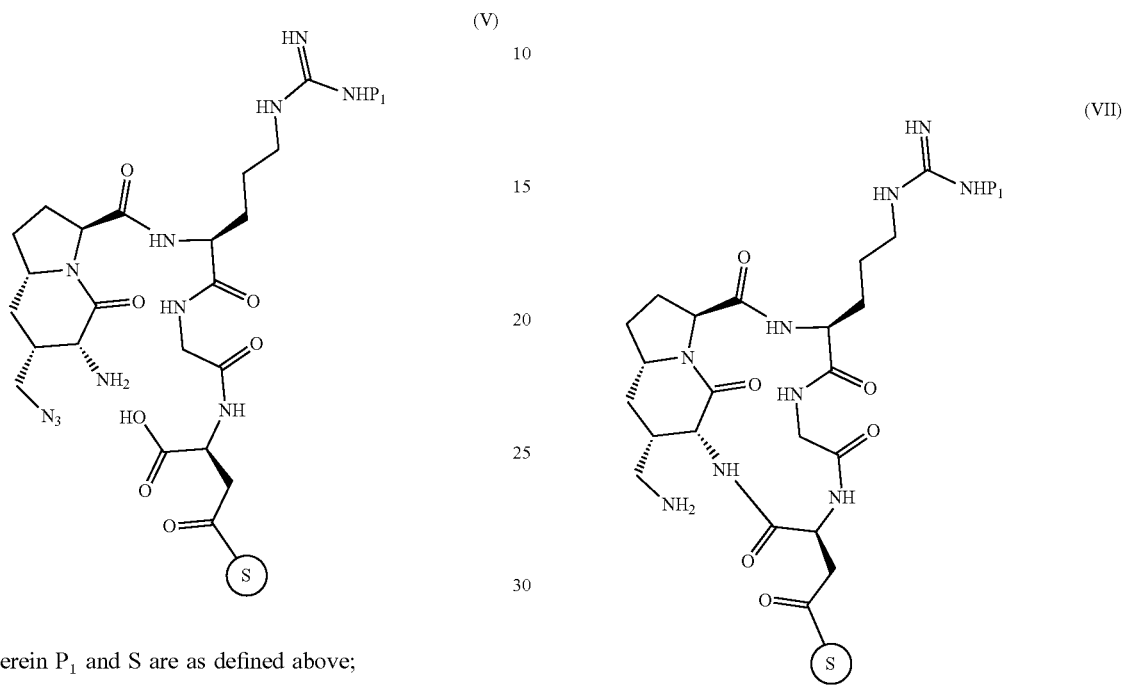

wherein P₁ and S are as defined above;

d) performing an intramolecular cyclization to provide a compound of formula (VI)

wherein P₁ and S are as defined above;

f) conjugating of the resulting compound of formula (VII) with a compound of formula (VIII)

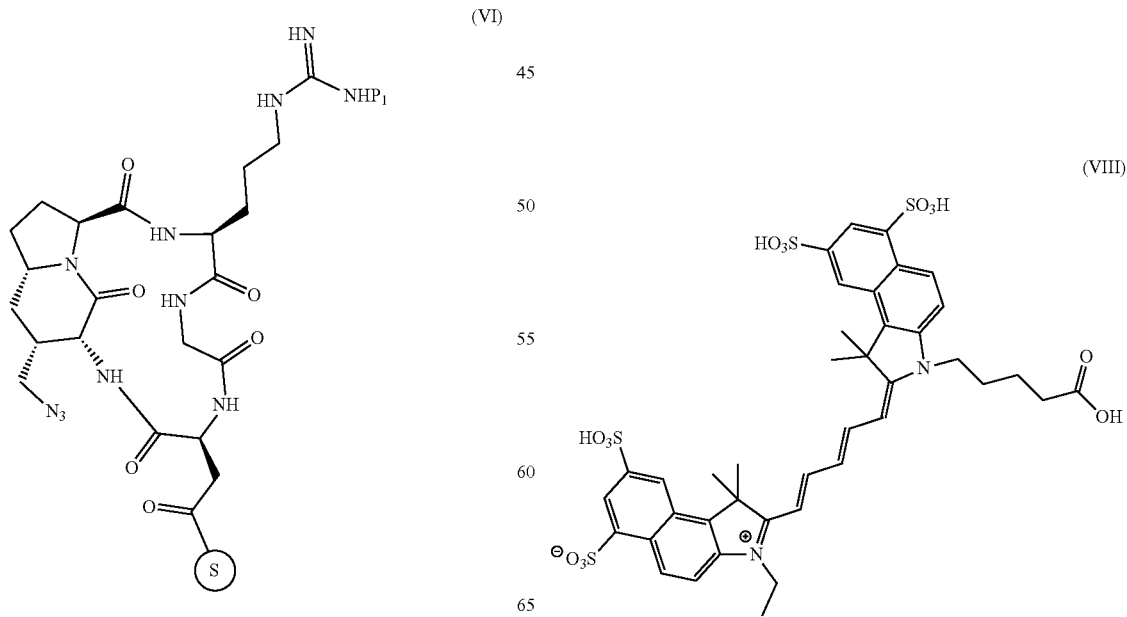

wherein P₁ and S are as defined above;

to obtain a compound of formula (IX)

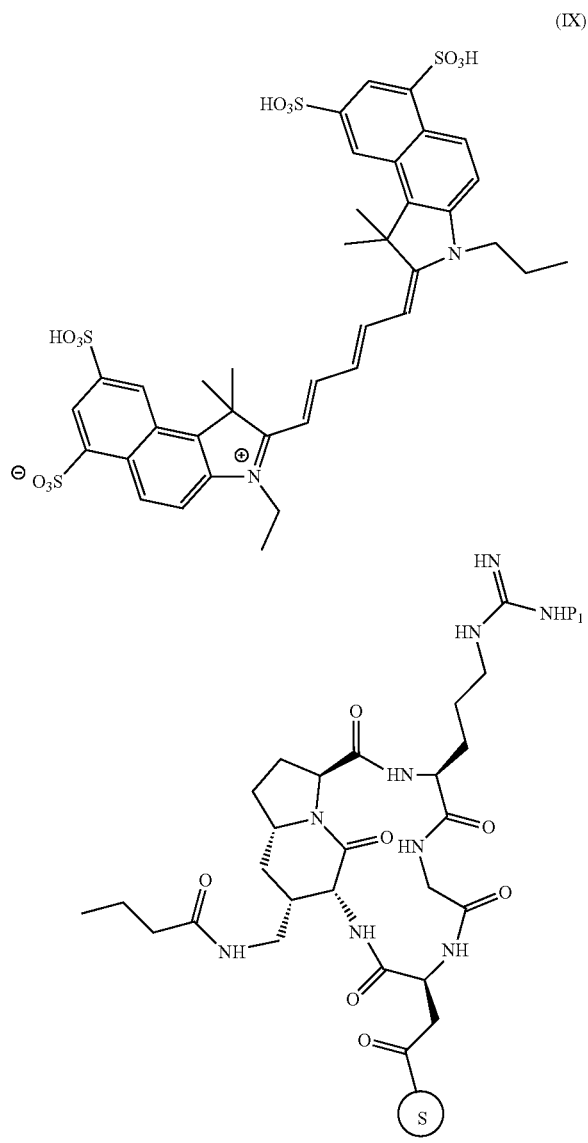

wherein $P_1$ and S are ad defined above;

g) removing the protecting group $P_1$ and cleavaging the peptido-like compound (IX) from the solid support S to obtain the compound of formula (I) as defined above.

2. The process according to claim 1, further comprising the steps of
h) purification of the compound of formula (I) obtained in step g), and optionally
i) lyophilization of the final product.

3. The process according to claim 1, wherein $P_1$ is a protecting group selected from 2,2,4,6,7-pentamethyl-2,3-dihydro-1-benzofuran-5-sulfonyl (Pbf), 2,3,6-trimethyl-4-methoxybenzene-sulfonyl (Mtr), p-toluenesulfonyl (Tos), trifluoroacetyl o-nitrobenzenesulfonyl (oNBS), 2,4-dinitrobenzenesulfonyl (dNBS), benzothiazole-2-sulfonyl (Bts), 2,2,5,7,8-pentamethylchroman-6-sulfonyl (Pmc) 2,3,6-trimethyl-4-methoxybenzene-sulfonyl (Mtr), p-toluenesulfonyl (Tos), trifluoroacetyl and tert-butyloxycarbonyl (Boc); $P_2$ is a protecting group selected from allyl, alkyl, t-butyl, trityl (Trt), 2,4-dimethoxybenzyl (DMB), benzyl (Bn), 9-fluorenylmethyl (Fm), 2-chlorotrityl (2-Cl-Trt), 2-phenylisopropyl (2-PhiPr), 5-phenyl-3,4-ethylenedioxythenyl derivatives (Phenyl-EDOTn), 4-(N-[1-(4,4-dimethyl-2,6-dioxocyclohexylidene)-3-methylbutyl]-amino)benzyl (Dmab), carbamoylmethyl (Cam), p-nitrobenzyl (pNB), 2-trimethylsilylethyl (TMSE), (2-phenyl-2-trimethylsiylyl)ethyl (PTMSE), 2-(trimethylsilyl)isopropyl (Tmsi), 2,2,2-trichloroethyl (Tce), p-hydroxyphenacyl, 4,5-dimethoxy-2-nitrobenzyl (Dmnb), 1,1-dimethylallyl (Dma), pentaamine cobalt (III), β-menthyl (Men), β-3-methylpent-3-yl (Mpe) and 4-(3,6,9-trioxadecyl)oxybenzyl (TEGBz or TEGBn); and $P_3$ is a protecting group selected from allyloxycarbonyl (alloc), benzyloxycarbonyl (Cbz), 2-(4-biphenyl)isopropyloxycarbonyl (Bpoc), 3,5-dimethoxyphenylisopropyloxycarbonyl (Ddz), 2-(4-nitrophenylsulfonyl)ethoxycarbonyl (Nsc), 1,1-dioxobenzo[b]thiophene-2-ylmethyloxycarbonyl (Bsmoc), (1,1-dioxonaphtho[1,2-b]thiophene-2-yl)methyloxycarbonyl (α-Nsmoc), 1-(4,4-dimethyl-2,6-dioxocyclohex-1-ylidene)-3-methylbutyl (ivDde), tetrachlorophthaloyl (TCP), 2-phenyl(methyl)sulfonio)ethyloxycarbonyltetrafluoroborate (Pms), ethanesulfonylethoxycarbonyl (Esc), 2-(4-sulfophenylsulfonyl)ethoxycarbonyl (Sps), trichloroethyloxycarbonyl (Troc), p-nitrobenzyloxycarbonyl (pNZ), propargyloxycarbonyl (Poc), o-nitrobenzyloxycarbonyl (oNZ), 4-nitroveratryloxycarbonyl (NVOC), (2-nitrophenyl)propyloxycarbonyl (NPPOC), azidomethyloxycarbonyl (Azoc) and trifluoroacetyl.

4. The process according to claim 3, wherein $P_1$ is 2,2,4,6,7-pentamethyl-2,3-dihydro-1-benzofuran-5-sulfonyl (Pbf), $P_2$ is allyl and $P_3$ is allyloxycarbonyl (Alloc).

5. The process according to claim 1, wherein the steps b), d) and f) are carried out in the presence of a coupling reagent and a base.

6. The process according to claim 5, wherein the coupling reagent is selected from the group consisting of N,N,N',N'-tetramethyl-O-(benzotriazol-1-yl)uronium tetrafluoroborate (TBTU), N,N,N',N'-tetramethyl-O-(1H-benzotriazol-1-yl)uronium hexafluorophosphate (HBTU), N,N,N',N'-tetramethyl-O-(7-azabenzotriazol-1-yl)uronium hexafluorophosphate (HATU), O-(1H-6-Chlorobenzotriazole-1-yl)-1,1,3,3-tetramethyluronium hexafluorophosphate (HCTU), 1-[1-(cyano-2-ethoxy-2-oxoethylidene-aminooxy)-dimethylamino-morpholino]-uronium hexafluorophosphate (COMU) and fluoro-N,N,N',N'-tetramethylformamidinium hexafluorophosphate (TFFH) and the base is a tertiary amine.

7. The process according to claim 6, wherein in step b) the coupling reagent is 1-[1-(cyano-2-ethoxy-2-oxoethylideneaminooxy)-dimethylamino-morpholino]-uronium hexafluorophosphate (COMU) and the base is N,N-diisopropylethylamine (DIPEA).

8. The process according to claim 6, wherein in step d) the coupling reagent is 7-azabenzotriazol-1-yloxy-tripyrrolidino-phosphonium hexafluorophosphate (PyAOP) and the base is N,N-diisopropylethylamine (DIPEA) and the ratio among the intermediate of formula (V), the coupling reagent and the base is about 1:1.5:3 (mol/mol).

9. The process according to claim 5, wherein the ratio between the intermediate of formula (II) and coupling reagent is about 1:2 (mol/mol); the ratio between the intermediate of formula (III) and the coupling reagent is about 1:0.98 (mol/mol); and the ratio between the intermediate of formula (III) and the N,N-diisopropylethylamine is about 1:2 (mol/mol).

10. The process according to claim 1, wherein the step c) is performed under Argon atmosphere with a prior activation phase of 3 min in the presence of an organosilane compound and a catalyst.

11. The process according to claim 10, wherein the organosilane is phenylsilane (PhSiH$_3$) and the catalyst is tetrakis(triphenylphosphine)palladium (0) (Pd(PPH$_3$)$_4$), and the ratio between the intermediate (IV) and the phenylsilane is about 1:25 (mol/mol).

12. The process according to claim 1, wherein step e) is carried out between 20° C. and 70° C., in the presence of an organophosphorous compound and water, for a period from 5 to 20 hours.

13. The process according to claim 1, wherein step f) is performed by prior activation of the intermediate of formula (VIII).

14. An intermediate compound of formula (III)

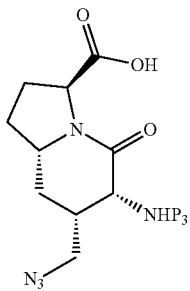
(III)

wherein P$_3$ is a protecting group.

15. The process according to claim 2, wherein P$_1$ is a protecting group selected from 2,2,4,6,7-pentamethyl-2,3-dihydro-1-benzofuran-5-sulfonyl (Pbf), 2,3,6-trimethyl-4-methoxybenzene-sulfonyl (Mtr), p-toluenesulfonyl (Tos), trifluoroacetyl o-nitrobenzenesulfonyl (oNBS), 2,4-dinitrobenzenesulfonyl (dNBS), benzothiazole-2-sulfonyl (Bts), 2,2,5,7,8-pentamethylchroman-6-sulfonyl (Pmc) 2,3,6-trimethyl-4-methoxybenzene-sulfonyl (Mtr), p-toluenesulfonyl (Tos), trifluoroacetyl and tert-butyloxycarbonyl (Boc); P$_2$ is a protecting group selected from allyl, alkyl, t-butyl, trityl (Trt), 2,4-dimethoxybenzyl (DMB), benzyl (Bn), 9-fluorenylmethyl (Fm), 2-chlorotrityl (2-Cl-Trt), 2-phenylisopropyl (2-PhiPr), 5-phenyl-3,4-ethylenedioxythenyl derivatives (Phenyl-EDOTn), 4-(N-[1-(4,4-dimethyl-2,6-dioxocyclohexylidene)-3-methylbutyl]-amino)benzyl (Dmab), carbamoylmethyl (Cam), p-nitrobenzyl (pNB), 2-trimethylsilylethyl (TMSE), (2-phenyl-2-trimethylsiylyl)ethyl (PTMSE), 2-(trimethylsilyl)isopropyl (Tmsi), 2,2,2-trichloroethyl (Tce), p-hydroxyphenacyl, 4,5-dimethoxy-2-nitrobenzyl (Dmnb), 1,1-dimethylallyl (Dma), pentaamine cobalt (III), β-menthyl (Men), β-3-methylpent-3-yl (Mpe) and 4-(3,6,9-trioxadecyl)oxybenzyl (TEGBz or TEGBn); and P$_3$ is a protecting group selected from allyloxycarbonyl (alloc), benzyloxycarbonyl (Cbz), 2-(4-biphenyl)isopropyloxycarbonyl (Bpoc), 3,5-dimethoxyphenylisopropyloxycarbonyl (Ddz), 2-(4-nitrophenylsulfonyl)ethoxycarbonyl (Nsc), 1,1-dioxobenzo[b]thiophene-2-ylmethyloxycarbonyl (Bsmoc), (1,1-dioxonaphtho[1,2-b]thiophene-2-yl)methyloxycarbonyl (α-Nsmoc), 1-(4,4-dimethyl-2,6-dioxocyclohex-1-ylidene)-3-methylbutyl (ivDde), tetrachlorophthaloyl (TCP), 2-phenyl(methyl)sulfonio)ethyloxycarbonyltetrafluoroborate (Pms), ethanesulfonylethoxycarbonyl (Esc), 2-(4-sulfophenylsulfonyl)ethoxycarbonyl (Sps), trichloroethyloxycarbonyl (Troc), p-nitrobenzyloxycarbonyl (pNZ), propargyloxycarbonyl (Poc), o-nitrobenzyloxycarbonyl (oNZ), 4-nitroveratryloxycarbonyl (NVOC), (2-nitrophenyl)propyloxycarbonyl (NPPOC), azidomethyloxycarbonyl (Azoc) and trifluoroacetyl.

16. The process according to claim 15, wherein P$_1$ is 2,2,4,6,7-pentamethyl-2,3-dihydro-1-benzofuran-5-sulfonyl (Pbf), P$_2$ is allyl and P$_3$ is allyloxycarbonyl (Alloc).

17. The process according to claim 13, wherein step f) is performed by prior activation of the intermediate of formula (VIII) with N,N-diisopropylethylamine (DIPEA) and 1-[1-(cyano-2-ethoxy-2-oxoethylidene-aminooxy)-dimethylamino-morpholino]-uronium hexafluorophosphate (COMU).

* * * * *